US005876708A

United States Patent [19]
Sachs

[11] Patent Number: 5,876,708
[45] Date of Patent: Mar. 2, 1999

[54] ALLOGENEIC AND XENOGENEIC TRANSPLANTATION

[75] Inventor: David H. Sachs, Newton, Mass.

[73] Assignee: The General Hospital Corporation, Boston, Mass.

[21] Appl. No.: 458,720

[22] Filed: Jun. 1, 1995

Related U.S. Application Data

[63] Continuation-in-part of Ser. No. 266,427, Jun. 27, 1994, Pat. No. 5,614,187, and Ser. No. 451,210, May 26, 1995, which is a continuation of Ser. No. 838,595, May 26, 1995, abandoned, and a continuation-in-part of Ser. No. 220,371, Mar. 29, 1994, abandoned, which is a continuation-in-part of PCT/US94/05527 May 16, 1994 Ser. No. 243,653, May 16, 1994, Pat. No. 5,685,564, Ser. No. 114,072, Aug. 30, 1993, Pat. No. 5,624,823, Ser. No. 150,739, Nov. 10, 1993, abandoned, and Ser. No. 212,228, Mar. 14, 1994, abandoned which is a continuation-in-part of PCT/US94/01616 Feb. 14, 1994..

[51] Int. Cl.$^6$ .............................. A61K 38/00; C12N 5/08
[52] U.S. Cl. .......................................... 424/93.1; 435/325
[58] Field of Search ............................... 424/93.1, 93.21; 435/32.5

[56] References Cited

U.S. PATENT DOCUMENTS

| 5,199,942 | 4/1993 | Gillis .......................................... 604/4 |
| 5,597,563 | 1/1997 | Beschorner ............................ 424/93.7 |

OTHER PUBLICATIONS

Asherson et al., "Adult thymectomy prevention of the appearance of suppressor T cells which depress contact sensitivity to picryl chloride and reversal of adult thymectomy effect by thymus extract" Eur. J. Immonol., 6:699–703 (1976).
Dick et al., "Genetic manipulation of hematopietic stem cells with retrovirus vectors", TIG Reviews, 2:165–170 (1986).
Fischel et al., "Prolonged Survival of Discordant Cardiac Xenograft in a Rhesus Monkey", Transpl. Proceedings, 23:589–590 (1991).
Green et al., "Extensive Prolongation of Rabbit Kidney Allograft Survival After Short–Term Cyclosporin–A Treatment", The Lancet, 1:1182–1183 (1978).
Lapidot et al., "Enhancement of bone marrow allografts from nude mice into mismatched recipients by T cell void of graft–versus–host activity", PNAS, 87:4595–4599 (1990).
Madsen et al., "Induction of Immunological Unresponsiveness Using Recipient Cells Transfected with Donor Class I or Class II MHC Genes", Transpl. Proceedings, 21:477 (1989).
Uhteg et al., "Cyclosporine–induced Transplantation Unresponsiveness in Rat Cardiac Allograft Recipients: In Vitro Determination of Helper and Suppressor Activity", J. Immunol., 135:1800–1805 (1985).
Bani–Sacchi et al., "Immunocytochemical and ultrastructural changes of islet cells in rats treated long–term with cyclosporine at immunotherapeutic doses," Transplantation, 49:982–987 (1990).
Beko II et al., "Mechanisms of prior blood tranfusion–cyclosporine–induced tolerance—A potential role for immune–cellular chimerism," Transplantation Proceedings, 23:147–148 (1991).
Bellgrau and Selawry, "Cyclosporine–Induced Tolerance to Intratesticular Islet Xenografts," Transplantation, 50:654–657 (1990).
Beschorner et al., "Transplant Tolerance Devleops after Cyclosporine," Laboratory Invest., 68:122a (1993).
Bom–van Noorlos et al., "Cyclosporine A in Orthotopic Porcine Liver Transplantation," Eur. Surg. Res., 16:329–335 (1984).
Borleffs et al., "Cyclosporin A as Optimal Immunosuppressant After Kidney Allografting in Rhesus Monkeys," Heart Transplantation, 2(2):111–117 (1983).
Calne et al., "Prolonged survival of pig orthotopic heart grafts treated with cyclosporin a," The Lancet, 1:1183–1184 (1978).
Cattral et al., "Transplantation of purfied single–donor canine islet allografts with cyclosporine," Transplantation, 47:583–587 (1989).
Collier et al., "Alternate–Day Cyclosporine A and Azathiprine in Experimental Dog Renal Allografts," Transplantation Proceedings, 19:1279–1280 (1987).
Cooper et al., "Effects of Cyclosporine and Antibody Adsorption on Pig Cardiac Xenograft Survival in the Baboon," J. Heart Transplantation, 7:238–246 (1988).
Davie et al., "Role of T Lymphocytes in the Humoral Immune Response," J. Immunol., 113:1438–1445 (1974).
Dugoni et al., "Evidence that Cyclosporine Prevents Rejection and Recurrent Diabetes in Pancreatic Transplants in the BB Rat," Transplantation, 49:845–848 (1990).
Fishbein, J. F. et al., "Development of Tolerance to Class II–Mismatched Renal Transplants after a Short Course of Cyclosporine Therapy in Miniature Swine," Transplantation, 57:1303–1308 (1994).
Fishbein, J. F. et al., "Interleukin–2 Reverses the Ability of Cyclosporine to Induce Tolerance to Class I Disparate Kidney Allografts in Miniature Swine," Transplantation Proceedings, 25:322–323 (1993).
Florack et al., "Effect of Short–Term High–Dose Cyclosporine Treatment on Endocrine Function of Segmental Pancreatic Grafts," Transplantation Proceedings, 23:1593–1595 (1991).
Flye, "Histologic Evidence of Modification of Liver Allograft Rejection in Inbred Miniature Swine by Cyclosporine," Transplantation Proceedings, 15:2983–2985 (1983).
Flye et al., "Prevention of Fatal Rejection of SLA–Mismatched Orthotopic Liver Allografts in Inbred Miniature Swine by Cyclosporin–A," Transplantation Proceedings, 15:1269–1271 (1983).

(List continued on next page.)

Primary Examiner—Jasemine C. Chambers
Assistant Examiner—Karen M. Hauda
Attorney, Agent, or Firm—Louis Myers, Esq.

[57] ABSTRACT

Methods of inducing tolerance including administering to the recipient a short course of help reducing treatment or administering a short course and methods of prolonging the acceptance of a graft by administering a short course of an immunosuppressant.

79 Claims, 4 Drawing Sheets

OTHER PUBLICATIONS

Fukuzawa et al., "Effect of cyclosporin A on T cell immunity I. Dose–dependent suppresion of different murine T helper cell pathways," *Eur. J. Immunol.*, 19:49–56 (1989).

Green et al., "Induction of Specific Tolerance in Rabbits by Kidney Allografting and Short Periods of Cyclosporin–A Treatment," *The Lancet*, 123–125 (21 Jul. 1979).

Guzzetta et al., "Induction of Kidney Tranplantation across Major Histocompatibility Complex Barriers by Bone Marrow Transplantation in Miniature Swine," *Transplantation*, 51:862–866 (1991).

Hall et al., "Suppressor T Cells in Rats with Prolonged Cardiac Allograft Survival after Treatment with Cyclosporine," *Tranplantation*, 37:595–600 (1984).

Hao et al., "Facilitation of Specific Tolerance Induction in Adult Mice by RS–61443," *Transplantation*, 53:590–595 (1992).

Hao et al., "Tolerance induction in adult mice cyclosporine inhibits RS–61443–induced tolerance," *Transplantation Proceedings*, 23:733–734 (1991).

Hess et al., "Immune mechanisms in cyclosporine–induced syngeneic graft–versus–host disease," *Transplantation*, 48:986–990 (1989).

Hutchinson et al., "Cyclosporin A Spares Selectivity Lymphocytes with Donor–Specific Suppressor Characteristics," *Transplantation*, 32:210–216 (1981).

Irschick et al., "Studies of the Mechanism of Tolerance Induced by Short–Term Immunosuppression with Cyclosporine in High–Risk Corneal Allograft Recipients," *Transplantation*, 48:986–990 (1989).

Kahan, "Medical Intelligence: drug therapy: cyclosporine," *N.E. J. Med.*, 321:1725–1738 (1989).

Kahan et al., "Important Role of Cyclosporine for the Induction of Immunologic Tolerance in Adult Hosts" *Tranplantation Proceedings*, 20(3 Suppl. 3):23–35 (Jun. 1988).

Kawahara et al., "Prolongation of heterotopic cardiac allografts in rats by cyclosporin A," *Surgery* 594–600 (Oct. 1980).

Ketchum et al., "Cyclosporine Therapy Concomitant with Renal Allotransplantation Induces Tolerance to Subsequent Door MHC–Identical Islet Grafts," *Transplantation Proceedings*, 24:899–900 (1992).

Kimball et al., "Mycophenolate Mofetil Reduces Human IGG Anti–ATGAM Antibody Formation" *14th Annual Meeting of the American Society of Tranplant Physicians*, Chicago, Illinois: 14–17 May 1995, p. 119 (Abstract No. 183).

Latinne et al., "Xenotransplantation from Pig to Cynomolgus Monkey: Approach Toward Tolerance Induction," *Tranplantation Proceedings*, 25:336–338 (1993).

Lim and Li, "Induction of tolerance to vascularised skin allografts using cyclosporin A—an experimental study on rats," *Ann. Acad. Med. Singapore*, 20:484–487 (1991).

Lim et al., "Steroid treatment depresses the production of tranplantation tolerance," *Tranplantation Proceedings*, 22:1989–1990 (1990).

Martin–Fontecha et al., "Transplantation of cultured thymic fragments in congenitally anthymic and euthymic rats," *Scand. J. Immunol.*, 35:575–587 (1992).

Moller et al., "Cellular Mechanisms Underlying Differential Rejection of Sequential Heart and Lung Allografts in Rats," *Tranplantation*, 55:650–655 (1993).

Morris and Jones, "Transplantation Versus Dialysis; A Study of Quality of Life," *Transplantation Proceedings*, 20:23–26 (1988).

Mottram et al., "T Suppressor Cells Induced by Tranfusion and Cyclosporine," *Tranplantation*, 50:1033–1037 (1990).

Neuhaus et al., "Results of Kidney Tranplantation in Rhesus Monkeys Treated with Cyclosporin A and Standard Immunosuppression," *Tranplantation Proceedings*, 14:111–112 (1982).

Norin et al., "Cyclosporin A as the Initial Immunosuppressive Agent for Canine Lung Transplantation," *Transplantation*, 34:372–375 (1982).

Norin et al., "Improved survival of transplanted lungs in mongrel dogs treated with cyclosporin a," *Tranplantation*, 32(3):259–260 (Sep. 1981).

Norin et al., "Unresponsiveness to Lung Allografts in Mongrel Dogs after Cessation of Cyclosporin–A Therapy," *Tranplantation Proceedings*, 15:508–510 (1983).

Odorico et al., "Promotion of Rat Cardiac Allograft Survival by Intrarhythmic Inoculation of Donor Spelnocytes," *Transplantation*, 55:1104–1107 (1993).

Oluwole et al., "Induction of Donor–Specific Unresponsiveness to Rat Cardiac Allograft by Donor Leukocytes and Cyclosporine," *Transplantation*, 45:1131–1135 (1988).

Pennington et al., "Bone Marrow Tranplantation in Miniature Swine," *Transplantation*, 45:21–26 (1988).

Pereira et al., "Mechanism of Action of Cyclosporine A In Vivo II. T. Cell Priming in Vivo to Alloantigen Can Be Mediated by an IL–2–Independent Cyclosporine A–Resistant Pathway," *J. Immunol.*, 144:2109–2116 (1990).

Reinsmoen et al., "A New In Vitro Approach to Determine Acquired Tolerance in Long–Term Kidney Allograft Recipients," *Transplantation*, 50:783–790 (1990).

Remuzzi et al., "Kidney graft survival in rats without immunosuppressants after intrarhythmic glomerular transplantation," *The Lancet*, 337:750–752 (30 Mar. 1991).

Rosengard et al., "The Failure of Skin Grafting to Break Tolerance to Class I–Disparate Renal Allografts in Miniature Swine Despite Inducing Marked Antidonor Cellular Immunity," *Transplantation*, 52:1044–1052 (1991).

Rosengard et al., "Induction of specific tolerance to class I–disparate renal allografts in miniature swine with cyclsoporine," *Transplantation*, 54(3):490–497 (1992).

Rosengard et al., "Renal Tranplantation in Miniature Swine: Preliminary Evidence That Graft Infiltrating Leukocytes Suppress Donor–Specific Cell–Mediated Lymphocytotoxicity in Co–Culture," *Tranplantation Proceedings*, 23:189–191 (1991).

Roslin et al., "One–Year Monkey Heart Xenograft Survival In Cyclosporine–Treated Baboons," *Transplantation*, 54:949–955 (1992).

Sachs and Bach, "Immunology of Xenograft Rejection," *Human Immunology*, 28:245–251 (1990).

Schreiber and Crabtree, "The mechanism of action of cyclosporin A and FK506," *Immunol. Today*, 13:136–142 (1992).

Sharabi and Sachs, "Mixed Chimerism and Permanent Specific Transplantation Tolerance Induced by a Nonlethal Preparative Regimen," *J. Exp. Med.*, 169:493–502 (1989).

Smith et al., "New Approaches to Tranplantation Tolerance" *Transplantation Proceedings*, 23:2157–2161 (1991).

Smith et al., "Sucessful Induction of Long–Term Specific Tolerance to Fully Allogeneic Renal Allografts in Miniature Swine," *Transplantation*, 53:438–444 (1992).

Stegall et al., "Pancreatic Islet Tranplantation in Cynomolgus Monkeys," *Tranplantation,* 48:944–950 (1989).

Sumrani et al., "Diabetes Mellitus After Renal Tranplantation in the Cyclosporine Era—An Analysis of Risk Factors," *Transplantation,* 51:343–347 (1991).

Tan et al., "Vascularized Muscle Allografts and the Role of Cyclosporine," *Plas. Recon. Surg.,* 87:412–418 (1991).

Tchervenkov et al., "The Effect of Donor–Specific Blood Transfusion, Cyclosporine, and Dietary Protaglandin Precursors on Rat Cardiac Allograft Survival," *Tranplantation,* 47:177–181 (1989).

Thomas et al., "Beneficial Effect of Cyclosporine in Post-transplantation Induction of Unresponsiveness of Renal Allografts in Rhesus Monkeys," *Transplantation Proceedings,* 20:134–136 (1988).

Thomas et al., "Long–term incompatible kidney survival in outbred higher primates without chronic immunosuppression," *Ann. Surg.,* 198:370–378 (1983).

Thomas et al., "Kidney Allograft Tolerance in Primates without Chronic Immunosuppression—The Role of Veto Cells," *Transplantation,* 51:198–207 (1991).

Uhteg et al., "Cyclosporine Induced Transplant Tolerance: Kinetics and Compartmentalization of Suppressor, Helper and NK Activity," *FASEB J.,* :F11, Abstract No. 3295 (1984).

Veith et al., "Cyclosporine A in Experimental Lung Tranplantation," *Transplantation,* 32:474–481 (1981).

White and Caine, "Cyclosporin a in heart allografting: its immunosuppresive and tolerance–inducing properties," *J. Heart Transplantation,* 1:102 (1982).

White et al., "Cyclsoporin–A–Induced Long–Term Survival of Fully Incompatible Skin and Heart Grafts in Rats," *Transplantation Proceedings,*12:261–265 (1980).

White et al., "Potential for Tolerance Induction with Cyclosporine," *Tranplantation Proceedings,* 15(4, Suppl. 1):2278–2286 (1983).

Thomas et al Ann Surg. 198: 370, 1988.

Smith et al Transpl. Proceedings 23(4): 2157, 1991.

Thomas et al Transpl. Proceedings 20:134, 1988.

Shandhi et al JEM 169:493; 1989.

Green et al The Lancet, 29 Jul. 1979, pp. 123–125.

Baliga et al. "CTLA41g prolongs allograft survival while suppressing cell–mediated immunity", Transplantation 58:1082–1090, 1994.

Madsen et al., "Immunological unrepsonsiveness induced by recipient cells transfected with donor MHC genes" Nature 332:161–164 10 Mar. 1988.

Mottram et al., "Increased expression of IL–4 and IL–10 and decreased expression IL–2 and interferon–$\lambda$ in long–surviving mouse heart allografts after brief CD4–monoclonal antibody therapy", Transplantation 59:559–565, 1995.

Pearson et al., "Induction of tranplantation tolerance in adults using donor antigen and anti–CD4 monoclonal antibody", Transplantation 54:475–483, 1992.

Sharabi et al., Specific Tolerance Induction Across a Xenogeneic Barrier: Production of Mixed Rat/Mouse lymphohematopoietic Chimeras Using a Nonlethal Preparative Regimen, J. Exp Med 172:195–202, 1909.

Sykes et al., "Bone marrow transplantation as a means of inducing tolerance" Seminars In Immunology 2:401–417, 1990.

Smith et al Transpl. Proceedings 23(4): 2157, 1991.

Schrecher et al. Immunology Today 13(4): 136, 1992.

Thomas et al. Tranpl. Proceedings 20(1): 134, 1988.

Thomas et al. Ann. Surg. 198(3): 370, 1983.

Kahin NEJM 321(25): 1725, 1989.

ALLOGENEIC AND XENOGENEIC TRANSPLANTATION

This application is a continuation-in-part of Ser. No. 08/266,427, filed Jun. 27, 1994, now issued as U.S. Pat. No. 5,614,187; and a continuation-in-part of Ser. No. 08/451,210, filed May 26, 1995, now pending which is a file wrapper continuation of Ser. No. 07/838,595, filed May 26, 1995, now abandoned; and a continuation-in-part of Ser. No. 08/220,371, filed Mar. 29, 1994, now abandoned; and a continuation-in-part of PCT/US94/05527, filed May 16, 1994, now completed; and a continuation-in-part of Ser. No. 08/243,653, filed May 16, 1994, now issued as U.S. Pat. No. 5,685,564; and a continuation-in-part of Ser. No. 08/114,072, filed Aug. 30, 1993, now issued as U.S. Pat. No. 5,624,823; and a continuation-in-part of Ser. No. 08/150,739, filed Nov. 10, 1993, now abandoned; and a continuation-in-part of Ser. No. 08/212,228, filed Mar. 14, 1994, now abandoned; and a continuation-in-part of PCT/US94/01616 filed Feb. 14, 1994, now completed.

BACKGROUND OF THE INVENTION

The invention relates to tissue and organ transplantation.

SUMMARY OF THE INVENTION

The invention provides several methods of inducing tolerance to foreign antigens, e.g., to antigens on allogeneic or xenogeneic tissue or organ grafts. These methods can be used individually or in combination with one another. For example, it has been found that the short-term administration of a help reducing agent, e.g., a short high dose course of cyclosporine A (CsA), can significantly prolong graft acceptance. The short term help reduction-methods of the invention can be combined with one or more other methods for prolonging graft acceptance. For example, a short course of high dose cyclosporine treatment to induce tolerance to unmatched donor class I and other minor unmatched donor antigens can be combined with implantation of retrovirally transformed bone marrow cells to induce tolerance to unmatched donor class II. A short course of high dose cyclosporine administered to induce tolerance to unmatched donor class I and other minor antigens can also be combined with implantation of donor bone marrow cells to induce tolerance to unmatched donor class II.

Accordingly, the invention features, in one aspect, a method of inducing tolerance in a recipient mammal, e.g., a primate, e.g., a human, to an allograft from a donor primate including: implanting the graft in the recipient; and administering to the recipient a short course of help reducing treatment, e.g., a short course of high dose cyclosporine. The short course of help reducing treatment is generally administered at about the time the graft is introduced into the recipient.

Preferably, the recipient is mismatched at a first locus which affects graft rejection, e.g., an MHC class I or II locus, or a minor antigen locus, and matched, or tolerant of a mismatch, at a second locus which affects graft rejection, e.g., an MHC class I or II locus, or a minor antigen locus. Matching at the second locus can be achieved by selection of a recipient or donor of the appropriate genotype. The recipient can be rendered tolerant of a mismatch at the second locus by any method of tolerance induction, e.g., by administering donor bone marrow tissue to the recipient to induce tolerance to donor antigens expressed on the donor bone marrow, by expressing an MHC antigen of the donor from a stem cell of the recipient to induce tolerance to the donor antigen, or by altering the immunological properties of the graft, e.g., by masking, cleaving, or otherwise modifying cell surface molecules on the graft. In preferred embodiments, any of the methods which can be used to match or induce tolerance to the second locus can be used to match or induce tolerance to a third locus which affects graft rejection, e.g., an MHC class I or II locus, or a minor antigen locus.

In preferred embodiments, the recipient and donor are matched at a class II locus and the short course of help reducing treatment induces tolerance to unmatched class I and/or minor antigens on the graft. In preferred embodiments, tolerance to a class II antigen is induced by a method other than a short course of a help reducing treatment, and the short course of help reducing treatment induces tolerance to unmatched class I and minor antigens on the graft.

In preferred embodiments, the duration of the short course of help reducing treatment is approximately equal to or is less than the period required for mature T cells of the recipient species to initiate rejection of an antigen after first being stimulated by the antigen (in humans this is usually 8–12 days, preferably about 10 days); in more preferred embodiments, the duration is approximately equal to or is less than two, three, four, five, or ten times the period required for mature T cells of the recipient to initiate rejection of an antigen after first being stimulated by the antigen.

In other preferred embodiments, the short course of help reducing treatment is administered in the absence of a treatment which stimulates the release of a cytokine by mature T cells in the recipient, e.g., in the absence of a steroid drug in a sufficient concentration to counteract the desired effect of the help reducing treatment, e.g., in the absence of Prednisone (17, 21-dihydroxypregna-1, 4-diene-3, 11, 20-trione) at a concentration which stimulates the release of a cytokine by mature T cells in the recipient. In preferred embodiments, the short course of help reducing treatment is administered in the absence of a steroid drug, e.g., in the absence of Prednisone.

In preferred embodiments: the help reducing treatment is begun before or at about the time the graft is introduced; the short course is perioperative, or the short course is postoperative; or the donor and recipient are class I matched.

Methods of inducing tolerance by a short-term administration of a help reducing agent, e.g., a short high dose course of cyclosporine A (CsA), can be combined with other methods for inducing tolerance, e.g., methods for the implantation of transduced bone marrow cells to induce tolerance to an antigen, e.g., the methods described in U.S. Ser. No. 008/126,122, filed on Sep. 23, 1993.

Accordingly, in another aspect, the invention features a method of inducing tolerance in a recipient mammal, e.g., a primate, e.g., a human, of a first species to a graft from a mammal, e.g., a swine, e.g., a miniature swine, of a second species, which graft preferably expresses a major histocompatibility complex (MHC) antigen. The method includes inserting DNA encoding an MHC antigen of the second species into a hematopoietic stem cell, e.g., a bone marrow hematopoietic stem cell, of the recipient mammal; allowing the MHC antigen encoding DNA to be expressed in the recipient; preferably, implanting the graft in the recipient; and, preferably, administering to the recipient a short course of help reducing treatment, e.g., a short course of high dose cyclosporine treatment. The short course of help reducing treatment is generally administered at about the time the graft is introduced into the recipient.

In preferred embodiments, the short course of help reducing treatment induces tolerance to unmatched class I and/or minor antigens on a graft which is introduced into the recipient subsequent to expression of the MHC antigen.

In preferred embodiments, the duration of the short course of help reducing treatment is approximately equal to or is less than the period required for mature T cells of the recipient species to initiate rejection of an antigen after first being stimulated by the antigen; in more preferred embodiments, the duration is approximately equal to or is less than two, three, four, five, or ten times the period required for a mature T cell of the recipient species to initiate rejection of an antigen after first being stimulated by the antigen.

In other preferred embodiments, the short course of help reducing treatment is administered in the absence of a treatment which stimulates the release of a cytokine by mature T cells in the recipient, e.g., in the absence of a steroid drug in a sufficient concentration to counteract the desired effect of the help reducing treatment, e.g., in the absence of Prednisone (17, 21-dihydroxypregna-1, 4-diene-3, 11, 20-trione) at a concentration which stimulates the release of a cytokine by mature T cells in the recipient. In preferred embodiments, the short course of help reducing treatment is administered in the absence of a steroid drug, e.g., in the absence of Prednisone.

In preferred embodiments: the help reducing treatment is begun before or at about the time the graft is introduced; the short course is perioperative; or the short course is postoperative.

Preferred embodiments include those in which: the cell is removed from the recipient mammal prior to the DNA insertion and returned to the recipient mammal after the DNA insertion; the DNA is obtained from the individual mammal from which the graft is obtained; the DNA is obtained from an individual mammal which is syngeneic with the individual mammal from which the graft is obtained; the DNA is obtained from an individual mammal which is MHC matched, and preferably identical, with the individual mammal from which the graft is obtained; the DNA includes an MHC class I gene; the DNA includes an MHC class II gene; the DNA is inserted into the cell by transduction, e.g., by a retrovirus, e.g., by a Moloney-based retrovirus; and the DNA is expressed in bone marrow cells and/or peripheral blood cells of the recipient for at least 14, preferably 30, more preferably 60, and most preferably 120 days, after the DNA is introduced into the recipient.

Other preferred embodiments include: the step of, prior to hematopoietic stem cell transplantation, creating hematopoietic space, e.g., by irradiating the recipient mammal with low dose, e.g., between about 100 and 400 rads, whole body irradiation to deplete or partially deplete the bone marrow of the recipient; inactivating thymic T cells by one or more of: prior to hematopoietic stem cell transplantation, irradiating the recipient mammal with, e.g., about 700 rads of thymic irradiation, or administering to the recipient a short course of an immunosuppressant, as is described herein.

Other preferred embodiments include: the step of, prior to implantation of a graft, depleting natural antibodies from the blood of the recipient mammal, e.g., by hemoperfusing an organ, e.g., a liver or a kidney, obtained from a mammal of the second species. (In organ hemoperfusion antibodies in the blood bind to antigens on the cell surfaces of the organ and are thus removed from the blood.)

In other preferred embodiments: the method further includes, prior to hematopoietic stem cell transplantation, introducing into the recipient an antibody capable of binding to mature T cells of said recipient mammal.

Other preferred embodiments further include the step of introducing into the recipient a graft obtained from the donor, e.g., a liver or a kidney.

In another aspect, the invention features a method of inducing tolerance in a recipient mammal, preferably a primate, e.g., a human, to a graft obtained from a donor of the same species, which graft preferably expresses an MHC antigen. The method includes: inserting DNA encoding an MHC antigen of the donor into a hematopoietic stem cell, e.g., bone marrow hematopoictic stem cell, of the recipient; allowing the MHC antigen encoding DNA to be expressed in the recipient; preferably, implanting the graft in the recipient; and, preferably, administering to the recipient a short course of help reducing treatment, e.g., a short course of high dose cyclosporine. The short course of help reducing treatment is generally administered at about the time the graft is introduced into the recipient.

In preferred embodiments, the short course of help reducing treatment induces tolerance to unmatched class I and/or minor antigens on a graft which is introduced into the recipient subsequent to expression of the MHC antigen.

In preferred embodiments, the duration of the short course of help reducing treatment is approximately equal to or is less than the period required for mature T cells of the recipient species to initiate rejection of an antigen after first being stimulated by the antigen; in more preferred embodiments, the duration is approximately equal to or is less than two, three, four, five, or ten times the period required for a mature T cell of the recipient species to initiate rejection of an antigen after first being stimulated by the antigen.

In other preferred embodiments, the short course of help reducing treatment is administered in the absence of a treatment which stimulates the release of a cytokine by mature T cells in the recipient, e.g., in the absence of a steroid drug in a sufficient concentration to counteract the desired effect of the help reducing treatment, e.g., in the absence of Prednisone (17, 21-dihydroxypregna-1, 4-diene-3, 11, 20-trione) at a concentration which stimulates the release of a cytokine by mature T cells in the recipient. In preferred embodiments, the short course of help reducing treatment is administered in the absence of a steroid drug, e.g., in the absence of Prednisone In preferred embodiments: the help reducing treatment is begun before or at about the time the graft is introduced; the short course is perioperative, or the short course is postoperative; or the donor and recipient are class I matched.

Preferred embodiments include those in which: the cell is removed from the recipient prior to the DNA insertion and returned to the recipient after the DNA insertion; the DNA includes a MHC class I gene; the DNA includes a MHC class II gene; the DNA is inserted into the cell by transduction, e.g. by a retrovirus, e.g., by a Moloney-based retrovirus; and the DNA is expressed in bone marrow cells and/or peripheral blood cells of the recipient at least 14, preferably 30, more preferably 60, and most preferably 120 days, after the DNA is introduced into the recipient.

In other preferred embodiments: the method further includes, prior to hematopoietic stem cell transplantation, introducing into the recipient an antibody capable of binding to mature T cells of said recipient mammal.

In preferred embodiments the graft is a liver or a kidney.

Other preferred embodiments include: the step of, prior to hematopoietic stem cell transplantation, creating hematopoietic space, e.g., by irradiating the recipient mammal with low dose, e.g., between about 100 and 400 rads, whole body irradiation to deplete or partially deplete the bone marrow of the recipient; inactivating thymic T cells by one or more of: prior to hematopoietic stem cell transplantation, irradiating the recipient mammal with, e.g., about 700 rads of thymic irradiation, or administering to the recipient a short course of an immunosuppressant, as is described herein.

Other preferred embodiments include: the step of, prior to implantation of a graft, depleting natural antibodies from the blood of the recipient mammal, e.g., by hemoperfusing an organ, e.g., a liver or a kidney, obtained from a mammal of the second species. (In organ hemoperfusion antibodies in the blood bind to antigens on the cell surfaces of the organ and are thus removed from the blood.)

Methods of inducing tolerance with a short-term administration of a help reducing agent, e.g., a short high dose course of cyclosporine A (CsA), can be combined with other methods for inducing tolerance, e.g., methods of inducing tolerance which use the implantation of donor stem cells to induce tolerance to an antigen, e.g., the methods described in U.S. Ser. No. 07/838,595, filed Feb. 19, 1992.

Accordingly, in another aspect, the invention features a method of inducing tolerance in a recipient mammal of a first species, e.g., a primate, e.g., a human, to a graft obtained from a mammal of a second, preferably discordant species, e.g., a swine, e.g., a miniature swine, or a discordant primate species. The method includes: preferably prior to or simultaneous with transplantation of the graft, introducing, e.g., by intravenous injection, into the recipient mammal, hematopoietic stem cells, e.g., bone marrow cells or fetal liver or spleen cells, of the second species (preferably the hematopoietic stem cells home to a site in the recipient mammal); (optionally) inactivating the natural killer cells of the recipient mammal, e.g., by prior to introducing the hematopoietic stem cells into the recipient mammal, introducing into the recipient mammal an antibody capable of binding to natural killer cells of said recipient mammal; preferably, implanting the graft in the recipient; and, preferably, administering to the recipient a short course of help reducing treatment, e.g., a short course of high dose cyclosporine. The short course of help reducing treatment is generally administered at the time at the graft is introduced into the recipient.

In preferred embodiments, the short course of help reducing treatment induces tolerance to unmatched class I and/or minor antigens on the graft which is introduced into the recipient.

In preferred embodiments, the duration of the short course of help reducing treatment is approximately equal to or is less than the period required for mature T cells of the recipient species to initiate rejection of an antigen after first being stimulated by the antigen; in more preferred embodiments, the duration is approximately equal to or is less than two, three, four, five, or ten times, the period required for a mature T cell of the recipient species to initiate rejection of an antigen after first being stimulated by the antigen.

In other preferred embodiments, the short course of help reducing treatment is administered in the absence of a treatment which stimulates the release of a cytokine by mature T cells in the recipient, e.g., in the absence of a steroid drug in a sufficient concentration to counteract the desired effect of the help reducing treatment, e.g., in the absence of Prednisone (17, 21-dihydroxypregna-1, 4-diene-3, 11, 20-trione) at a concentration which stimulates the release of a cytokine by mature T cells in the recipient. In preferred embodiments, the short course of help reducing treatment is administered in the absence of a steroid drug, e.g., in the absence of Prednisone.

In preferred embodiments: the help reducing treatment is begun before or at about the time the graft is introduced; or the short course is perioperative, the short course is postoperative.

As will be explained in more detail below, the hematopoietic cells prepare the recipient for the graft that follows, by inducing tolerance at both the B-cell and T-cell levels. Preferably, hematopoietic cells are fetal liver or spleen, or bone marrow cells, including immature cells (i.e., undifferentiated hematopoietic stem cells; these desired cells can be separated out of the bone marrow prior to administration), or a complex bone marrow sample including such cells can be used.

One source of anti-NK antibody is anti-human thymocyte polyclonal anti-serum. As is discussed below, preferably, a second anti-mature T cell antibody can be administered as well, which lyses T cells as well as NK cells. Lysing T cells is advantageous for both bone marrow and xenograft survival. Anti-T cell antibodies are present, along with anti-NK antibodies, in anti-thymocyte anti-serum. Repeated doses of anti-NK or anti-T cell antibody may be preferable. Monoclonal preparations can be used in the methods of the invention.

Other preferred embodiments include: the step of introducing into the recipient mammal, donor species-specific stromal tissue, preferably hematopoietic stromal tissue, e.g., fetal liver or thymus. In preferred embodiments: the stromal tissue is introduced simultaneously with, or prior to, the hematopoietic stem cells; the hematopoietic stem cells are introduced simultaneously with, or prior to, the antibody.

Other preferred embodiments include those in which: the same mammal of the second species is the donor of one or both the graft and the hematopoietic cells; and the antibody is an anti-human thymocyte polyclonal anti-serum, obtained, e.g., from a horse or pig.

Other preferred embodiments include: the step of, prior to hematopoietic stem cell transplantation, creating hematopoietic space, e.g., by irradiating the recipient mammal with low dose, e.g., between about 100 and 400 rads, whole body irradiation to deplete or partially deplete the bone marrow of the recipient; inactivating thymic T cells by one or more of: prior to hematopoietic stem cell transplantation, irradiating the recipient mammal with, e.g., about 700 rads of thymic irradiation, or administering to the recipient a short course of an immunosuppressant, as is described herein.

Other preferred embodiments include: the step of, prior to hematopoietic stem cell transplantation, depleting natural antibodies from the blood of the recipient mammal, e.g., by hemoperfusing an organ, e.g., a liver or a kidney, obtained from a mammal of the second species. (In organ hemoperfusion antibodies in the blood bind to antigens on the cell surfaces of the organ and are thus removed from the blood.)

In other preferred embodiments: the method further includes, prior to hematopoietic stem cell transplantation, introducing into the recipient an antibody capable of binding to mature T cells of said recipient mammal.

In other preferred embodiments: the method further includes inactivating T cells of the recipient, e.g., by, prior to introducing the hematopoietic stem cells into the recipient, introducing into the recipient an antibody capable of binding to T cells of the recipient.

In preferred embodiments, the method includes the step of introducing into the recipient a graft obtained from the donor which is obtained from a different organ than the hematopoietic stem cells, e.g., a liver or a kidney.

In another aspect, the invention features a method of inducing tolerance in a recipient mammal, preferably a primate, e.g., a human, to a graft obtained from a donor, e.g., of the same species. The method includes: preferably prior to or simultaneous with transplantation of the graft, introducing, e.g., by intravenous injection, into the recipient, hematopoietic stem cells, e.g., bone marrow cells or fetal liver or spleen cells, of a mammal, preferably the donor (preferably the hematopoietic stem cells home to a site in the recipient); (optionally), inactivating T cells of the recipient, e.g., by, prior to introducing the hematopoietic stem cells into the recipient, introducing into the recipient an antibody capable of binding to T cells of the recipient; preferably, implanting the graft in the recipient; and, preferably, administering to the recipient a short course of help reducing treatment, e.g., a short course of high dose cyclosporine. The short course of help reducing treatment is generally administered at the time the graft is introduced into the recipient.

In preferred embodiments, the short course of help reducing treatment induces tolerance to unmatched class I and minor antigens on the graft which is introduced into the recipient.

In preferred embodiments, the duration of the short course of help reducing treatment is approximately equal to or is less than the period required for mature T cells of the recipient species to initiate rejection of an antigen after first being stimulated by the antigen; in more preferred embodiments, the duration is approximately equal to or is less than two, three, four, five, or ten times the period required for a mature T cell of the recipient species to initiate rejection of an antigen after first being stimulated by the antigen.

In other preferred embodiments, the short course of help reducing treatment is administered in the absence of a treatment which stimulates the release of a cytokine by mature T cells in the recipient, e.g., in the absence of a steroid drug in a sufficient concentration to counteract the desired effect of the help reducing treatment, e.g., in the absence of Prednisone (17,21-dihydroxypregna-1,4-diene-3, 11, 20-trione) at a concentration which stimulates the release of a cytokine by mature T cells in the recipient. In preferred embodiments, the short course of help reducing treatment is administered in the absence of a steroid drug, e.g., in the absence of Prednisone In preferred embodiments: the help reducing treatment is begun before or at about the time the graft is introduced; the short course is perioperative, the short course is postoperative; the donor and recipient are class I matched.

In preferred embodiments, the hematopoietic stem cells are introduced simultaneously with, or prior to administration of the antibody; the antibody is an antihuman thymocyte polyclonal anti-serum; and the anti-serum is obtained from a horse or pig.

Other preferred embodiments include: the further step of, prior to hematopoietic stem cell transplantation, inactivating or depleting NK cells of the recipient, e.g., by introducing into the recipient mammal an antibody capable of binding to NK cells of the recipient mammal; and those in which the same individual is the donor of both the graft and the bone marrow.

Other preferred embodiments include: the step of, prior to hematopoietic stem cell transplantation, creating hematopoietic space, e.g., by irradiating the recipient mammal with low dose, e.g., between about 100 and 400 rads, whole body irradiation to deplete or partially deplete the bone marrow of the recipient; inactivating thymic T cells by one or more of, prior to hematopoietic stem cell transplantation, irradiating the recipient mammal with, e.g., about 700 rads of thymic irradiation, or administering to the recipient a short course of an immunosuppressant, as is described herein.

Other preferred embodiments include: the further step of, prior to bone marrow transplantation, absorbing natural antibodies from the blood of the recipient by hemoperfusing an organ, e.g., the liver, or a kidney, obtained from the donor.

Preferred embodiments include: the step of introducing into the recipient mammal, donor species specific stromal tissue, preferably hematopoietic stromal tissue, e.g., fetal liver or thymus.

In preferred embodiments, the method includes the step of introducing into the recipient, a graft which is obtained from a different organ than the hematopoietic stem cells, e.g., a liver or a kidney.

Methods of inducing tolerance with short-term administration of a help reducing agent, e.g., a short high dose course of cyclosporine A (CsA), can be combined with yet other methods for inducing tolerance, e.g., with: methods which use the implantation of a xenogeneic thymic graft to induce tolerance, e.g., the methods described in U.S. Ser. No. 08/163, 912 filed on Dec. 7, 1993; methods of increasing the level of the activity of a tolerance promoting or GVHD inhibiting cytokine or decreasing the level of activity of a tolerance inhibiting or GVHD promoting cytokine, e.g., the methods described in U.S. Ser. No. 08/114,072, filed Aug. 30, 1993; methods of using cord blood cells to induce tolerance, e.g., the methods described in U.S. Ser. No. 08/150,739 filed Nov. 10, 1993; and the methods for inducing tolerance disclosed in Sykes and Sachs, PCT/US94/01616, filed Feb. 14, 1994.

It has also been discovered that a short course of an immunosuppressant, e.g., cyclosporine, can be used to diminish or inhibit T cell activity which would otherwise promote the rejection of an allograft or xenograft.

Accordingly, in another aspect, the invention features a method of diminishing or inhibiting T cell activity, preferably the activity of thymic or lymph node T cells, in a recipient mammal, erg., a primate, e.g., a human, which receives a graft from a donor mammal. The method includes, inducing tolerance to the graft; administering to the recipient a short course of an immunosuppressive agent, e.g., cyclosporine, sufficient to inactivate T cells, preferably thymic or lymph node T cells; and preferably transplanting the graft into the recipient.

Tolerance to the graft can be induced by any method, e.g., by any of the methods discussed herein. For example, tolerance can be induced by the administration of donor allogeneic or xenogeneic hematopoietic stem cells, the administration of genetically engineered autologous stem cells, by the administration of a short course of a help reducing agent, or by altering the immunological properties of the graft, e.g., by masking, cleaving, or otherwise modifying cell surface molecules of the graft.

In preferred embodiments the duration of the short course of immunosuppressive agent is: approximately equal to 30 days; approximately equal to or less than 8–12 days, preferably about 10 days; approximately equal to or less than two, three, four, five, or ten times the 8–12 or 10 day period.

In preferred embodiments: the short course is begun before or at about the time the treatment to induce tolerance is begun, e.g., at about the time, xenogeneic, allogeneic, genetically engineered syngeneic, or genetically engineered autologous stem cells are introduced into the recipient; the short course begins on the day the treatment to induce tolerance is begun, e.g., on the day, xenogeneic, allogeneic, genetically engineered syngeneic, or genetically engineered autologous stem cells are introduced into the recipient; the short course begins within 1, 2, 4, 6, 8, or 10 days before or after the treatment to induce tolerance is begun, e.g., within 1, 2, 4, 6, 8, or 10 days before or after xenogeneic, allogeneic, genetically engineered syngeneic, or genetically engineered autologous stem cells are introduced into the recipient.

In other preferred embodiments: the short course of an immunosuppressive is administered in conjunction with an anti-T cell antibody; the short course of an immunosuppressive is sufficient to inactivate T cells, e.g., thymic or lymph node T cells, which would not be inactivated by antibody-based inactivation of T cells, e.g., inactivation by intravenous administrations of ATG antibody, or similar, preparations.

In preferred embodiments: the recipient mammal is other than a mouse or rat.

Methods of inactivating T cells, preferably thymic or lymph node T cells, of the invention can be combined with methods of inducing tolerance in which the inactivation of T cells is desirable. The anti-T cell methods of the invention can be used in place of, or in addition to, methods for the inactivation of T cells called for, or useful in such methods of inducing tolerance. For example, anti-thymic or lymph node T cell methods of the invention can be used with methods for the implantation of transduced bone marrow cells to induce tolerance to an antigen, e.g., the methods described in U.S. Ser. No. 008/126,122, filed on Sep. 23, 1993.

Accordingly, in another aspect, the invention features a method of promoting, in a recipient mammal of a first species, the acceptance of a graft from a donor mammal of a second species, which graft, preferably, expresses a major histocompatibility complex (MHC) antigen. The method includes inserting DNA encoding an MHC antigen of the second species into a hematopoietic stem cell, e.g., a bone marrow hematopoietic stem cell, of the recipient mammal; allowing the MHC antigen encoding DNA to be expressed in the recipient; and, preferably, administering to the recipient a short course of an immunosuppressive agent, e.g., a short course of cyclosporine treatment, sufficient to inactivate recipient T cells, preferably thymic or lymph node T cells. (Thymic or lymph node T cells might otherwise inhibit the survival of the graft or engineered cells.)

In preferred embodiments, the duration of the short course of immunosuppressive agent is: approximately equal to 30 days; approximately equal to or less than 8–12 days, preferably about 10 days; approximately equal to or less than two, three, four, five, or ten times the 8–12 or 10 day period.

In preferred embodiments: the recipient mammal is a primate, e.g., a human, and the donor mammal is a swine, e.g., a miniature swine.

In preferred embodiments: the short course is begun before or at about the time genetically engineered stem cells are introduced into the recipient; the short course begins on the day the genetically engineered stem cells are introduced into the recipient; the short course begins within 1, 2, 4, 6, 8, or 10 days before or after the genetically engineered stem cells are introduced into the recipient.

In other preferred embodiments: the short course of an immunosuppressive agent is administered in conjunction with an anti-T cell antibody; the short course of immunosuppressive is sufficient to inactivate T cells, e.g., thymic or lymph node T cells, which would not be inactivated by antibody-based inactivation of T cells, e.g., inactivation by intravenous administrations of ATG, or similar, antibody preparations.

Preferred embodiments include those in which: the cell is removed from the recipient mammal prior to the DNA insertion and returned to the recipient mammal after the DNA insertion; the DNA is obtained from the individual mammal from which the graft is obtained; the DNA is obtained from an individual mammal which is syngeneic with the individual mammal from which the graft is obtained; the DNA is obtained from an individual mammal which is MHC matched, and preferably identical, with the individual mammal from which the graft is obtained; the DNA includes an MHC class I gene; the DNA includes an MHC class II gene; the DNA is inserted into the cell by transduction, e.g., by a retrovirus, e.g., by a Moloney-based retrovirus; and the DNA is expressed in bone marrow cells and/or peripheral blood cells of the recipient for at least 14, preferably 30, more preferably 60, and most preferably 120 days, after the DNA is introduced into the recipient.

Other preferred embodiments include: the step of, prior to hematopoietic stem cell implantation, creating hematopoietic space in the recipient so as to promote engraftment and survival of the implanted stem cells, e.g., by irradiating the recipient mammal with low dose, e.g., between about 100 and 400 rads, whole body irradiation to deplete or partially deplete the bone marrow of the recipient.

In preferred embodiments, the method further includes the administration of thymic irradiation to the recipient, e.g., 700 rads of thymic irradiation.

Other preferred embodiments include: the step of depleting natural antibodies from the blood of the recipient mammal, e.g., by hemoperfusing an organ, e.g., a liver or a kidney, obtained from a mammal of the second species. (In organ hemoperfusion antibodies in the blood bind to antigens on the cell surfaces of the organ and are thus removed from the blood.)

Other preferred embodiments further include the step of introducing into the recipient a graft obtained from the donor, e.g., a liver or a kidney.

In another aspect, the invention features a method of promoting, in a recipient mammal, preferably a primate, e.g., a human, acceptance of a graft obtained from a donor of the same species, which graft expresses an MHC antigen. The method includes: inserting DNA encoding an MHC antigen of the donor into a hematopoietic stem cell, e.g., a bone marrow hematopoietic stem cell, of the recipient; allowing the MHC antigen encoding DNA to be expressed in the recipient; and, preferably, administering to the recipient a short course of an immunosuppressive agent, e.g., a short course of cyclosporine treatment, sufficient to inactivate recipient T cells, preferably thymic or lymph node T cells. (Thymic or lymph node T cells might otherwise inhibit the survival of the graft or engineered cells.)

In preferred embodiments, the duration of the short course of immunosuppressive agent is: approximately equal to 30 days; approximately equal to or less than 8–12 days, preferably about 10 days; approximately equal to or less than two, three, four, five, or ten times the 8–12 or 10 day period.

In preferred embodiments: the short course is begun before or at about the time genetically engineered stem cells are introduced into the recipient; the short course begins on the day the genetically engineered stem cells are introduced into the recipient; the short course begins within 1, 2, 4, 6, 8, or 10 days before or after the genetically engineered stem cells are introduced into the recipient.

In other preferred embodiments: the short course of an immunosuppressive agent is administered in conjunction with an anti-T cell antibody; the short course of immunosuppressive is sufficient to inactivate T cells, e.g., thymic or lymph node T cells, which would not be inactivated by antibody-based inactivation of T cells, e.g., inactivation by intravenous administrations of ATG, or similar, antibody preparations.

Preferred embodiments include those in which: the cell is removed from the recipient prior to the DNA insertion and returned to the recipient after the DNA insertion; the DNA includes a MHC class I gene; the DNA includes a MHC class II gene; the DNA is inserted into the cell by transduction, e.g. by a retrovirus, e.g., by a Moloney-based retrovirus; and the DNA is expressed in bone marrow cells and/or peripheral blood cells of the recipient at least 14, preferably 30, more preferably 60, and most preferably 120 days, after the DNA is introduced into the recipient.

Other preferred embodiments include: the step of, prior to hematopoietic stem cell implantation, creating hematopoietic space in the recipient so as to promote engraftment and survival of the implanted stem cells, e.g., by irradiating the recipient mammal with low dose, e.g., between about 100 and 400 rads, whole body irradiation to deplete or partially deplete the bone marrow of the recipient.

In preferred embodiments, the method further includes the administration of thymic irradiation to the recipient, e.g., 700 rads of thymic irradiation.

Other preferred embodiments include: the step of depleting natural antibodies from the blood of the recipient mammal, e.g., by hemoperfusing an organ, e.g., a liver or a kidney, obtained from a mammal of the second species. (In organ hemoperfusion antibodies in the blood bind to antigens on the cell surfaces of the organ and are thus removed from the blood.) Other preferred embodiments further include the step of introducing into the recipient a graft obtained from the donor, e.g., a liver or a kidney.

Methods of inactivating T cells, preferably thymic or lymph node T cells, of the invention can be combined with methods of inducing tolerance which use the implantation of donor stem cells to induce tolerance to an antigen, e.g., the methods described in U.S. Ser. No. 07/838,595, filed Feb. 19, 1992, hereby incorporated by reference.

Accordingly, in another aspect, the invention features a method of promoting, in a recipient mammal of a first species, e.g., a primate, e.g., a human, acceptance of a graft obtained from a mammal of a second, preferably discordant species, e.g., a swine, e.g., a miniature swine, or a discordant primate species. The method includes: introducing, e.g., by intravenous injection, into the recipient mammal, hematopoietic stem cells, e.g., bone marrow cells or fetal liver or spleen cells, of the second species (preferably the hematopoietic stem cells home to a site in the recipient mammal); (optionally) inactivating natural killer cells of the recipient mammal, e.g., by, prior to introducing the hematopoietic stem cells into the recipient mammal, introducing into the recipient mammal an antibody capable of binding to natural killer cells of said recipient mammal; (optionally) inactivating T cells of the recipient mammal, e.g., by, prior to introducing the hematopoietic stem cells into the recipient mammal, introducing into the recipient mammal an antibody capable of binding to T cells of the recipient mammal; and, preferably, administering to the recipient a short course of an immunosuppressive agent, e.g., a short course of cyclosporine treatment, sufficient to inactivate recipient T cells, preferably thymic or lymph node T cells. (Thymic or lymph node T cells might otherwise inhibit the engraftment or survival of the engineered cells.)

In preferred embodiments, the duration of the short course of immunosuppressive agent is: approximately equal to 30 days; approximately equal to or less than 8–12 days, preferably about 10 days; approximately equal to or less than two, three, four, five, or ten times the 8–12 or 10 day period mentioned above.

In preferred embodiments: the short course is begun before or at about the time stem cells are introduced into the recipient; the short course begins on the day the stem cells are introduced into the recipient; the short course begins within 1, 2, 4, 6, 8, or 10 days before or after the stem cells are introduced into the recipient.

In other preferred embodiments: the short course of an immunosuppressive agent is administered in conjunction with one or both of an anti-T cell antibody, or thymic irradiation, e.g., 700 rads of thymic irradiation; the short course of immunosuppressive is sufficient to inactivate T cells, e.g., thymic or lymph node T cells, which would not be inactivated by antibody-based inactivation of T cells, e.g., inactivation by intravenous administrations of ATG antibody preparations.

As will be explained in more detail below, the hematopoietic cells prepare the recipient for the graft that follows, by inducing tolerance at both the B-cell and T-cell levels. Preferably, hematopoietic cells are fetal liver or spleen, or bone marrow cells, including immature cells (i.e., undifferentiated hematopoietic stem cells; these desired cells can be separated out of the bone marrow prior to administration), or a complex bone marrow sample including such cells can be used.

One source of anti-NK antibody is anti-human thymocyte polyclonal anti-serum. As is discussed below, preferably, a second anti-mature T cell antibody can be administered as well, which lyses T cells as well as NK cells. Lysing T cells is advantageous for both bone marrow and xenograft survival. Anti-T cell antibodies are present, along with anti-NK antibodies, in anti-thymocyte anti-serum. Repeated doses of anti-NK or anti-T cell antibody may be preferable. Monoclonal preparations can be used in the methods of the invention.

Other preferred embodiments include: the step of introducing into the recipient mammal, donor species-specific stromal tissue, preferably hematopoietic stromal tissue, e.g., fetal liver or thymus. In preferred embodiments: the stromal tissue is introduced simultaneously with, or prior to, the hematopoietic stem cells; the hematopoietic stem cells are introduced simultaneously with, or prior to, an anti-NK or T cell antibody.

Other preferred embodiments include those in which: the same mammal of the second species is the donor of one or both the graft and the hematopoietic cells; and the anti-T or anti-NK cell antibody is an anti-human thymocyte polyclonal anti-serum, obtained, e.g., from a horse or pig.

Other preferred embodiments include: the step of, prior to hematopoietic stem cell transplantation, creating hematopoietic space in the recipient so as to promote engraftment and survival of the implanted stem cells, e.g., by irradiating the recipient mammal with low dose, e.g., between about 100 and 400 rads, whole body irradiation to deplete or partially deplete the bone marrow of the recipient.

In preferred embodiments, the method further includes the administration of thymic irradiation to the recipient, e.g., 300 to 700 rads of thymic irradiation.

Other preferred embodiments include: the step of prior to hematopoietic stem cell transplantation, depleting natural antibodies from the blood of the recipient mammal, e.g., by hemoperfusing an organ, e.g., a liver or a kidney, obtained from a mammal of the second species. (In organ hemoperfusion antibodies in the blood bind to antigens on the cell surfaces of the organ and are thus removed from the blood.)

Other preferred embodiments further include the step of introducing into the recipient a graft obtained from the donor, e.g., a graft which is obtained from a different organ than the hematopoietic stem cells, e.g., a liver or a kidney.

In preferred embodiments the stem cells are introduced into the recipient prior to or simultaneous with transplantation of the graft.

In another aspect, the invention features a method of promoting, in a recipient mammal, preferably a primate, e.g., a human, acceptance of a graft obtained from a donor of the same species. The method includes: introducing, e.g., by intravenous injection into the recipient, hematopoietic stem cells, e.g., bone marrow cells or fetal liver or spleen cells, of a mammal, preferably the donor (preferably the hematopoietic stem cells home to a site in the recipient); (optionally) inactivating T cells of the recipient, e.g., by, prior to introducing the hematopoietic stem cells into the recipient, introducing into the recipient an antibody capable of binding to T cells of the recipient; and, preferably, administering to the recipient a short course of an immunosuppressive agent, e.g., a short course of cyclosporine treatment, sufficient to inactivate recipient T cells, preferably thymic or lymph node T cells. (Thymic or lymph node T cells might otherwise inhibit the engraftment or survival of the engineered cells.)

In preferred embodiments, the duration of the short course of immunosuppressive agent is: approximately equal to 30 days; approximately equal to or less than 8–12 days, preferably about 10 days; approximately equal to or less than two, three, four, five, or ten times the 8–12 or 10 day period mentioned above.

In preferred embodiments: the short course is begun before or at about the time stem cells are introduced into the recipient; the short course begins on the day the stem cells are introduced into the recipient; the short course begins within 1, 2, 4, 6, 8, or 10 days before or after the stem cells are introduced into the recipient.

In other preferred embodiments: the short course of an immunosuppressive agent is administered in conjunction with one or both of an anti-T cell antibody, or thymic irradiation, e.g., 700 rads of thymic irradiation; the short course of immunosuppressive is sufficient to inactivate T cells, e.g., thymic or lymph node T cells, which would not be inactivated by antibody-based inactivation of T cells, e.g., inactivation by intravenous administrations of ATG antibody preparations.

In preferred embodiments, the anti-T cell or NK cell antibody is an antihuman thymocyte polyclonal anti-serum; and the anti-serum is obtained from a horse or pig.

Other preferred embodiments include: the further step of, prior to hematopoietic stem cell transplantation, inactivating recipient NK cells, e.g., by introducing into the recipient mammal an antibody capable of binding to NK cells of the recipient mammal; and those in which the same individual is the donor of both the graft and the bone marrow.

Other preferred embodiments include: the step of, prior to hematopoietic stem cell transplantation, creating hematopoietic space in the recipient so as to promote engraftment and survival of the implanted stem cells, e.g., by irradiating the recipient mammal with low dose, e.g., between about 100 and 400 rads, whole body irradiation to deplete or partially deplete the bone marrow of the recipient.

In preferred embodiments the method further includes administering thymic irradiation to the recipient, e.g., 700 rads of thymic irradiation.

Other preferred embodiments include: the further step of, prior to bone marrow transplantation, absorbing natural antibodies from the blood of the recipient by hemoperfusing an organ, e.g., the liver, or a kidney, obtained from the donor.

Preferred embodiments include: the step of introducing into the recipient mammal, donor species specific stromal tissue, preferably hematopoietic stromal tissue, e.g., fetal liver or thymus.

Other preferred embodiments further include the step of introducing into the recipient, a graft obtained from the donor, e.g., a graft which is obtained from a different organ than the hematopoietic stem cells, e.g., a liver or a kidney.

In preferred embodiments, the stem cells are introduced into the recipient prior to or simultaneous with transplantation of the graft.

Methods of inactivating T cells, preferably thymic or lymph node T cells, of the invention can be used with yet other methods of inducing tolerance in which the inactivation of thymic or lymph node T cells is desirable. For example, anti-thymic or lymph node T cell methods of the invention can be used with: methods which use the implantation of a xenogeneic thymic graft to induce tolerance, e.g., the methods described in U.S. Ser. No. 08/163, 912 filed on Dec. 7, 1993; methods of increasing the level of the activity of a tolerance promoting or GVHD inhibiting cytokine or decreasing the level of activity of a tolerance inhibiting or GVHD promoting cytokine, e.g., the methods described in U.S. Ser. No. 08/114,072, filed Aug. 30, 1993; methods of using cord blood cells to induce tolerance, e.g., the methods described in U.S. Ser. No. 08/150,739; and the methods for inducing tolerance disclosed in Sykes and Sachs, PCT/US94/01616, filed Feb. 14, 1994.

"An immunosuppressive agent capable of inactivating thymic or lymph node T cells", as used herein, is an agent, e.g., a chemical agent, e.g., a drug, which, when administered at an appropriate dosage, results in the inactivation of thymic or lymph node T cells. Examples of such agents are cyclosporine, FK-506, and rapamycin. Anti-T cell antibodies, because they are comparatively less effective at inactivating thymic or lymph node T cells, are not preferred for use as agents. An agent should be administered in sufficient dose to result in significant inactivation of thymic or lymph node T cells which are not inactivated by administration of an anti-T cell antibody, e.g., an anti-ATG preparation. Putative agents, and useful concentrations thereof, can be prescreened by in vitro or in vivo tests, e.g., by administering the putative agent to a test animal, removing a sample of thymus or lymph node tissue, and testing for the presence of active T cells in an in vitro or in vivo assay. Such prescreened putative agents can then be further tested in transplant assays.

"Short course of a immunosuppressive agent", as used herein, means a transitory non-chronic course of treatment. The treatment should begin before or at about the time the treatment to induce tolerance is begun, e.g., at about the time, xenogeneic, allogeneic, genetically engineered syngeneic, or genetically engineered autologous stem cells are introduced into the recipient. e.g., the short course can begin on the day the treatment to induce tolerance is begun, e.g., on the day, xenogeneic, allogeneic, genetically engineered syngeneic, or genetically engineered autologous stem cells are introduced into the recipient or the short course can begin within 1, 2, 4, 6, 8, or 10 days before or after the treatment to induce tolerance is begun, e.g., within 1, 2, 4, 6, 8, or 10 days before or after xenogeneic, allogeneic, genetically engineered syngeneic, or genetically engineered autologous stem cells are introduced into the recipient. The short course can last for: a period equal to or less than about 8–12 days, preferably about 10 days, or a time which is approximately equal to or is less than two, three, four, five, or ten times the 8–12 or 10 day period. Optimally, the short course lasts about 30 days. The dosage should be sufficient to maintain a blood level sufficient to inactivate thymic or lymph node T cells. A dosage of approximately 15 mg/kg/day has been found to be effective in primates.

"Lymph node or thymic T cell", as used herein, refers to T cells which are resistant to inactivation by traditional methods of T cell inactivation, e.g., inactivation by a single intravenous administration of anti-T cell antibodies, e.g., anti-bodies, e.g., ATG preparation.

"Help reduction", as used herein, means the reduction of T cell help by the inhibition of the release of at least one cytokine, e.g., any of IL-2, IL-4, IL-6, gamma interferon, or TNF, from T cells of the recipient at the time of the first exposure to an antigen to which tolerance is desired. The inhibition induced in a recipient's T cell secretion of a cytokine must be sufficient such that the recipient is tolerized to an antigen which is administered during the reduction of help. Although not being bound by theory, it is believed that the level of reduction is one which substantially eliminates the initial burst of IL-2 which accompanies the first recognition of a foreign antigen but which does not eliminate all mature T cells, which cells may be important in educating and producing tolerance.

"A help reducing agent", as used herein, is an agent, e.g., an immunosuppressive drug, which results in the reduction of cytokine release. Examples of help reducing agents are cyclosporine, FK-506, and rapamycin. Anti-T cell antibodies, because they can eliminate T cells, are not preferred for use as help reducing agents. A help reducing agent must be administered in sufficient dose to give the level of inhibition of cytokine release which will result in tolerance. The help reducing agent should be administered in the absence of treatments which promote cytokine, e.g., IL-2, release. Putative agents help reducing agents can be prescreened by in vitro or in vivo tests, e.g., by contacting the putative agent with T cells and determining the ability of the treated T cells to release a cytokine, e.g., IL-2. The inhibition of cytokine release is indicative of the putative agent's efficacy as a help reducing agent. Such prescreened putative agents can then be further tested in a kidney transplant assay. In a kidney transplant assay a putative help reducing agent is tested for efficacy by administering the putative agent to a recipient monkey and then implanting a kidney from a class II matched class I and minor antigen mismatched donor monkey into the recipient. Tolerance to the donor kidney (as indicated by prolonged acceptance of the graft) is indicative that the putative agent is, at the dosage tested, a help reducing agent.

"Short course of a help reducing agent", as used herein, means a transitory non-chronic course of treatment. The treatment should begin before or at about the time of transplantation of the graft. Alternatively, the treatment can begin before or at about the time of the recipient's first exposure to donor antigens. Optimally, the treatment lasts for a time which is approximately equal to or less than the period required for mature T cells of the recipient species to initiate rejection of an antigen after first being stimulated by the antigen. The duration of the treatment can be extended to a time approximately equal to or less than two, three, four, five, or ten times, the period required for a mature T cell of the recipient species to initiate rejection of an antigen after first being stimulated by the antigen. The duration will usually be at least equal to the time required for mature T cells of the recipient species to initiate rejection of an antigen after first being stimulated by the antigen. In pigs and monkeys, about 12 days of treatment is sufficient. Experiments with cyclosporine A (10 mg/kg) in pigs show that 6 days is not sufficient. Other experiments in monkeys show that IL-2 administered on day 8, 9, or 10 of cyclosporine A treatment will result in rejection of the transplanted tissue. Thus, 8, 9, or 10 days is probably not sufficient in pigs. In monkeys, a dose of 10 mg/kg cyclosporine with a blood level of about 500–1,000 ng/ml is sufficient to induce tolerance to class II matched class I and minor antigen mismatched kidneys. The same blood level, 500–1,000 ng/ml, is sufficient to induce tolerance in pigs. Long-term administration of 5 mg/kg prevents rejection (by long term immune suppression) but does not result in tolerance 0.

"Tolerance", as used herein, refers to the inhibition of a graft recipient's immune response which would otherwise occur, e.g., in response to the introduction of a nonself MHC antigen into the recipient. Tolerance can involve humoral, cellular, or both humoral and cellular responses.

"Hematopoietic stem cell", as used herein, refers to a cell, e.g., a bone marrow cell which is capable of developing into a mature myeloid and/or lymphoid cell Stem cells derived from the cord blood of the recipient or the donor can be used in methods of the invention. See U.S. Pat. No. 5,192,553, hereby incorporated by reference, and U.S. Pat. No. 5,004,681, hereby incorporated by reference.

"MHC antigen", as used herein, refers to a protein product of one or more MHC genes; the term includes fragments or analogs of products of MHC genes which can evoke an immune response in a recipient organism. Examples of MHC antigens include the products (and fragments or analogs thereof) of the human MHC genes, i.e., the HLA genes. MHC antigens in swine, e.g., miniature swine, include the products (and fragments and analogs thereof) of the SLA genes, e.g., the DRB gene.

"Miniature swine", as used herein, refers to wholly or partially inbred animal.

"Graft", as used herein, refers to a body part, organ, tissue, or cells. Grafts may consist of organs such as liver, kidney, heart or lung; body parts such as bone or skeletal matrix; tissue such as skin, intestines, endocrine glands; or progenitor stem cells of various types.

"A discordant species combination", as used herein, refers to two species in which hyperacute rejection occurs when a graft is grafted from one to the other. Generally, discordant species are from different orders, while non-discordant species are from the same order. For example, rats and mice are non-discordant species, i.e. their MHC antigens are substantially similar, and they are members of the same order, rodentia.

"Stromal tissue", as used herein, refers to the supporting tissue or matrix of an organ, as distinguished from its functional elements or parenchyma.

The help suppressing methods of the invention avoid the undesirable side effects of long-term or chronic administration of the broad spectrum immune suppressants often used in transplantation. Long-term or chronic administration of drugs such as Prednisone, Imuran, CyA, and, most recently FK506, have all had an important impact on the field of transplantation. However, all of these drugs cause nonspecific suppression of the immune system which must be titrated sufficiently to avoid rejection while not completely eliminating immune function. Patients who must stay on chronic immunosuppressive therapy for the remainder of their lives face major complications arising from too much or too little immunosuppression, causing infection and rejection, respectively. The help suppressing methods of the invention are based on the administration of a transitory short term high dose course of a help reducing treatment.

Recipient thymic or lymph node T cells are responsible for significant resistance to implanted grafts, e.g., to transplanted hematopoietic cells or transplanted organs. It has been found that the usual methods of T cell depletion or inactivation, e.g., the administration of anti-T cell antibodies, often fall short of an optimum level of T cell depletion or inactivation. In particular, such methods fail to provide optimum levels of depletion or inactivation of thymic or lymph node T cells. Methods of the invention in which a short course of an immunosupressant, e.g., cyclosporine, capable of inactivating recipient thymic or lymph node T cells is administered to the recipient, result in more thorough inactivation of thymic or lymph node T cells and thus in improved acceptance of graft tissue.

The retroviral methods of the invention allow the reconstitution of a graft recipient's bone marrow with transgenic autologous bone marrow cells expressing allogeneic or xenogeneic MHC genes. Expression of the transgenic MHC genes confers tolerance to grafts which exhibit the products of these or closely related MHC genes. Thus, these methods provide for the induction of specific transplantation tolerance by somatic transfer of MHC genes. Retroviral methods of the invention avoid the undesirable side effects of broad spectrum immune suppressants which are often used in transplantation.

Tolerance to transplantation antigens can be achieved through induction of lymphohematopoietic chimerism by bone marrow transplantation (BMT). BMT across MHC barriers presents two major risks: if mature T cells are not removed from the marrow inoculum the recipient may develop severe graft versus host disease (GVHD); removal of these cells often leads to failure of engraftment. Retroviral methods of the invention, which induce specific tolerance by reconstitution of the recipient's bone marrow with autologous (as opposed to allogeneic or heterologous) bone marrow cells, allow tolerance to be conferred with minimal risk of GVHD and with minimal need to remove T cells from the marrow inoculum.

Retroviral methods of the invention can be combined with the help suppression and T cell inactivation methods of the invention to prolong graft acceptance.

Hematopoietic cell transplant methods of the invention avoid the undesirable side effects of broad spectrum immune suppressants which are often used in transplantation. Hematopoietic cell transplant methods of the invention can be combined with the help suppression and T cell elimination methods of the invention to prolong graft acceptance.

Other features and advantages of the invention will be apparent from the following detailed description, and from the claims.

DETAILED DESCRIPTION

The drawings will first be briefly described.

Drawings

FIGS. 8a–d are diagrams of FACS analysis of thymocytes from graft rejectors, and controls.

Figure 9:
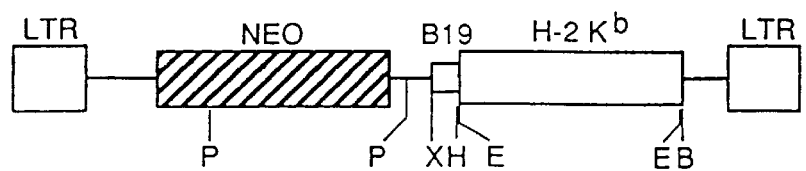

FIG. 9 is a diagram of the N2-B19-H2b vector.

OVERVIEW

The invention provides several methods of inducing tolerance to foreign antigens, e.g., to antigens on allogeneic or xenogeneic tissue or organ grafts. These methods can be used individually or in combination. For example, it has been discovered that short-term administration of a help reducing agent, e.g., a short high dose course of cyclosporine A (CsA) significantly prolongs graft acceptance. (Preferably the help reduction regime of the invention substantially eliminates the initial burst of IL-2 which accompanies the first recognition of an antigen but does not eliminate mature T cells. This is distinct from anti-T cell antibody treatments which eliminate mature T cells.)

It has also been discovered that a short course of an immunosuppressant, e.g., cyclosporine, can be used to inactivate T cells which would otherwise promote the rejection of a graft.

The help suppression methods of the invention can be combined with other methods for prolonging graft acceptance. Section I below discusses implantation of retrovirally transformed bone marrow cells to induce tolerance to MHC disparity. This method can be combined with help suppression methods of the invention, e.g., a short course of high dose of cyclosporine to induce tolerance to class I and other minor disparities.

Section II below discusses implantation of bone marrow cells to induce tolerance to MHC disparity. This method can be combined with a short course of high dose cyclosporine administration to induce tolerance to class I and other minor disparities. A short course of cyclosporine, to eliminate T cells, can also be combined with bone marrow transplant.

I. A short course of high dose cyclosporine (administered in the absence of treatments which stimulate the release of cytokines e.g. the absence of Prednisone) to induce tolerance to class I and other minor disparities combined with implantation of retrovirally transformed bone marrow cells to induce tolerance to class II disparity.

Retroviral transformation

Retroviral transformation allows the reconstitution of a graft recipient's bone marrow with transgenic bone marrow cells, preferably autologous bone marrow cells, expressing allogeneic or xenogeneic MHC genes. Expression of the transgenic MHC genes confers tolerance to grafts which exhibit the products of these or closely related MHC genes. Thus, these methods provide for the induction of specific transplantation tolerance by somatic transfer of MHC genes. Retroviral introduction of M14C genes can be used alone or combined with the T cell help reducing methods described herein. This approach is discussed in detail below.

MHC Genes: MHC genes for a variety of species are well studied. For example the HLA genes in man, see, e.g., Hansen et al., 1989, The Major Histocompatibility Complex, In *Fundamental Immunology* 2d ed., W. E. Paul, ed., Raven Press Ltd., New York, hereby incorporated by reference, and the SLA genes in swine, see e.g., Sachs et al., 1988, *Immunogenetics* 28:22–29, hereby incorporated by reference, have been cloned and characterized.

A gene encoding a MHC antigen can be used in methods of the invention to confer tolerance to a graft which displays that or a closely related MHC antigen. Methods of the invention can be used to confer tolerance to allogeneic grafts, e.g., wherein both the graft donor and the recipient are humans, and to xenogeneic grafts, e.g., wherein the graft donor is a nonhuman animal, e.g., a swine, e.g., a miniature swine, and the graft recipient is a human.

The individual which supplies the MHC genes should be as genetically similar as possible, particularly in terms of the MHC genes, to the individual which supplies the graft. For example, in allogeneic grafts wherein the implant donor is a human and the implant recipient is a human it is preferable to use MHC genes from the donor. In this embodiment, MHC probes, e.g., a probe from a third person or a synthetic consensus probe, can be used to isolate DNA encoding the MHC gene or genes of the implant donor individual. This allows the closest match between the genes used to confer tolerance and the genes which express MHC antigens on the graft.

In xenogeneic grafts, the implant donor individual, and the individual which supplies the tolerance conferring DNA should be the same individual or should be as closely related as possible. For example, it is preferable to derive implant tissue from a colony of donors which is highly inbred and, more preferably, which is homozygous for the MHC genes. This allows the single cloned MHC sequence to be used for many graft recipients.

Transformation of bone marrow cells: MHC genes can be introduced into bone marrow cells by any methods which allows expression of these genes at a level and for a period sufficient to confer tolerance. These methods include e.g., transfection, electroporation, particle gun bombardment, and transduction by viral vectors, e.g., by retroviruses.

Recombinant retroviruses are a preferred delivery system. They have been developed extensively over the past few years as vehicles for gene transfer, see e.g., Eglitis et al., 1988, *Adv. Exp. Med. Biol.* 241:19. The most straightforward retroviral vector construct is one in which the structural genes of the virus are replaced by a single gene which is then transcribed under the control of regulatory elements contained in the viral long terminal repeat (LTR). A variety of single-gene-vector backbones have been used, including the Moloney murine leukemia virus (MoMuLV). Retroviral vectors which permit multiple insertions of different genes such as a gene for a selectable marker and a second gene of interest, under the control of an internal promoter can be derived from this type of backbone, see e.g., Gilboa, 1988, *Adv. Exp. Med. Biol.* 241:29.

The elements of the construction of vectors for the expression of a protein product, e.g., the choice of promoters is known to those skilled in the art. The most efficient expression from retroviral vectors is observed when "strong" promoters are used to control transcription, such as the SV 40 promoter or LTR promoters, reviewed in Chang et al., 1989, *Int. J Cell Cloning* 7:264. These promoters are constitutive and do not generally permit tissue-specific expression. However, in the case of class I genes, which are normally expressed in all tissues, ubiquitous expression is acceptable for functional purposes. Housekeeping gene promoters, e.g., the thymidine kinase promoter, are appropriate promoters for the expression of class II genes.

The use of efficient packaging cell lines can increase both the efficiency and the spectrum of infectivity of the produced recombinant virions, see Miller, 1990, *Human Gene Therapy* 1:5. Murine retroviral vectors have been useful for transferring genes efficiently into murine embryonic, see e.g., Wagner et al., 1985, *EMBO J.* 4:663; Griedley et al., 1987 *Trends Genet.* 3:162, and hematopoietic stem cells, see e.g., Lemischka et al., 1986, *Cell* 45:917–927; Dick et al., 1986, *Trends in Genetics* 2:165–170.

A recent improvement in retroviral technology which permits attainment of much higher viral titers than were previously possible involves amplification by consecutive transfer between ecotropic and amphotropic packaging cell lines, the so-called "ping-pong" method, see e.g., Kozak et al., 1990, *J. Virol.* 64:3500–3508; Bodine et al., 1989, *Prog. Clin. Biol. Res.* 319: 589–600.

Transduction efficiencies can be enhanced by preselection of infected marrow prior to introduction into recipients, enriching for those bone marrow cells expressing high levels of the selectable gene, see e.g., Dick et al., 1985, *Cell* 42:71–79; Keller et al., 1985, *Nature* 318:149–154. In addition, recent techniques for increasing viral titers permit the use of virus-containing supernatants rather than direct incubation with virus-producing cell lines to attain efficient transduction, see e.g., Bodine et al., 1989, *Prog. Clin. Biol. Res.* 319:589–600. Because replication of cellular DNA is required for integration of retroviral vectors into the host genome, it may be desirable to increase the frequency at which target stem cells which are actively cycling e.g., by inducing target cells to divide by treatment in vitro with growth factors, see e.g., Lemischka et al., 1986, *Cell* 45:917–927, a combination of IL-3 and IL-6 apparently being the most efficacious, see e.g., Bodine et al., 1989, *Proc. Natl. Acad. Sci.* 86:8897–8901, or to expose the recipient to 5-fluorouracil, see e.g., Mori et al., 1984, *Jpn. J Clin. Oncol.* 14 Suppl. 1:457–463, prior to marrow harvest, see e.g., Lemischka et al., 1986, *Cell* 45:917–927; Chang et al., 1989, *Int. J. Cell Cloning* 7:264–280.

N2A or other Moloney-based vectors are preferred retroviral vectors for transducing human bone marrow cells.

Preparative Regimen For The Introduction of Transformed Bone Marrow Cells To prepare for bone marrow cells the recipient must undergo an ablation of the immune response which might otherwise resist engraftment.

The preparative regimens necessary to permit engraftment of modified autologous hematopoietic stem cells may be much less toxic than those needed for allogeneic bone marrow transplantation—preferably requiring only depletion of mature T cells with monoclonal antibodies, as has been recently demonstrated in a mouse model, see Sharabi et al., 1989, *J. Exp. Med.* 169:493–502. It is possible that transient expression may be sufficient to induce tolerance, which may then be maintained by the transplant even if expression on hematopoietic cells is lost, as has been observed for heart transplants in a mixed xenogeneic bone marrow transplant model, Ildstad et al., 1985, *Transplant. Proc.* 17: 535–538.

Graft and help reduction: The help reducing methods described above can be administered in conjunction with transplantation of the graft, as is described above.

Sustained expression of a swine class II gene in murine bone marrow hematopoietic cells by retroviral-mediated gene transfer Overview: The efficacy of a gene transfer approach to the induction of transplantation tolerance in miniature swine model was shown by using double-copy retroviral vectors engineered to express a drug-resistance marker (neomycin)

and a swine class II DRB cDNA. Infectious particles containing these vectors were produced at a titer of >1×10⁶ G418-resistant colony-forming units/ml using both ecotropic and amphotropic packaging cell lines. Flow cytometric analysis of DRA-transfected murine fibroblasts subsequently transduced with virus-containing supernatants demonstrated that the transferred sequences were sufficient to produce DR surface expression. Cocultivation of murine bone marrow with high-titer producer lines leads to the transduction of 40% of granulocyte/macrophage colony-forming units (CFU-GM) as determined by the frequency of colony formation under G418 selection. After nearly 5 weeks in long-term bone marrow culture, virus-exposed marrow still contained G418-resistant CFU-GM at a frequency of 25%. In addition, virtually all of the transduced and selected colonies contained DRB-specific transcripts. These results show that a significant proportion of very primitive myelopoietic precursor cells can be transduced with the DRB recombinant vector and that vector sequences are expressed in the differentiated progeny of these cells. These experiments are described in detail below.

Construction and Screening of SLA-DRB Recombinant Retroviruses As in man, Lee et al., 1982, *Nature* 299:750–752, Das et al., 1983, *Proc. Natl. Acad. Sci. USA* 80:3543–3547, the sequence of the swine DRA gene is minimally polymorphic. Therefore, transduction of allogeneic DRB cDNAs into bone marrow cells should be sufficient to allow expression of allogeneic class II DR molecules on cells committed to express this antigen.

Figure 1:
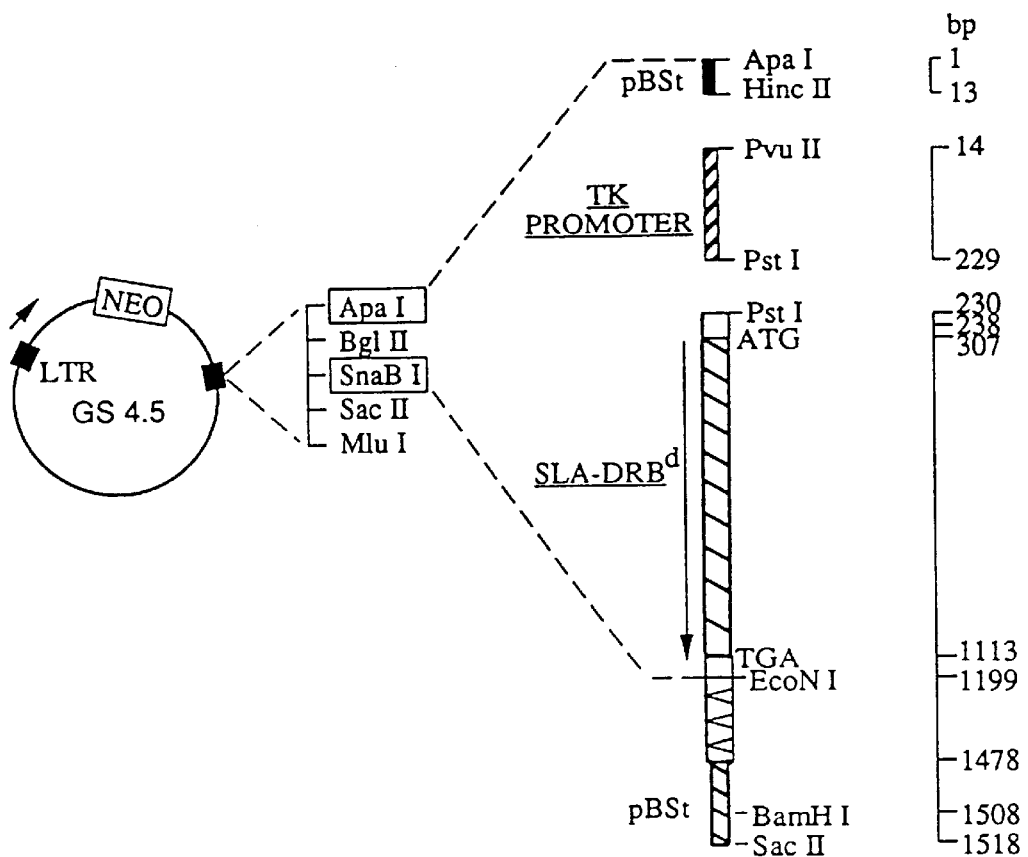
FIG. 1 is a diagram of the GS4.5 retroviral construct.

Details of retroviral constructs are given in FIG. 1. Two types of retroviral constructs, GS4.4 and GS4.5, were prepared. The diagram in FIG. 1 depicts the GS4.5 retroviral construct. The arrows in FIG. 1 indicate the directions of transcription. In GS4.5, the orientation of DRB cDNA transcription is the same as viral transcription. In GS4.4 (not shown), the TK promoter and the DRB cDNA were inserted into the 3' LTR of N2A in the reverse orientation of transcription with respect to viral transcription and the simian virus 40 3' RNA processing signal was added. pBSt refers to Bluescript vector sequence (Stratagene). The thymidine kinase (TK) promoter was contained within the 215-base-pair (bp) Pvu II-Pst I fragment from the herpes simplex virus TK gene, McKnight, 1980 *Nucleic Acids Res.* 8:5949–5964. The simian virus 40 3' RNA processing signal was contained within the 142 bp Hpa I-Sma I fragment from the pBLCAT3 plasmid, Luckow et al., (1987) *Nucleic Acids Res.* 15:5490–5497, (see FIG. 1). Sequence analysis of the junctions of the promoter, the class II cDNA, and the vector sequences confirmed that the elements of the constructs were properly ligated.

These retroviral constructs were transfected into the amphotropic packaging cell line PA317, and transfectants were selected in G418-containing medium. A total of 24 and 36 clones, transfected, respectively, with the GS4.4 and GS4.5 recombinant plasmids, were tested by PEG precipitation of culture supernatants and slot-blot analysis of viral RNA. Of these, 8 and 12 clones were found, respectively, to be positive for DRB, although the DRB signal was consistently weaker for the GS4.4-derived clones. Analysis of genomic and spliced transcripts from GS4.5 cells by dot-blot analysis of PEG-precipitated particles revealed heterogeneity among viral transcripts in various clones transfected by GS4.5. In one experiment, two clones contained DRB⁺/Neo+ viral RNA, two contained DRB⁺/Neo⁻ RNA, two contained DRB⁻/Neo⁺ RNA, and one showed no class II or Neo signal. G418-resistance (G418$_r$) titer determination of supernatants from DRB-positive clones confirmed that the average titer produced by GS4.5-transfected clones (10³–10⁴ CFU/ml) was significantly higher than that of the GS4.4-transfected clones (10²–10³ CFU/ml). Further transduction experiments were, therefore, conducted with the best clone, named GS4.5 C4, which produced an initial G418$^r$ titer of 3×10⁴ CFU/ml.

Plasmid preparation, cloning procedures, DNA sequencing, RNA preparations, Northern blots, and RNA slot blots were performed by standard methods, Sambrook et al., 1989, *Molecular Cloning: A Laboratory Manual* 2nd Ed. (Cold Spring Harbor Lab., Cold Spring Harbor). Final washes of blots were carried out in 0.1×SSPE (1×SSPE= 0.18M NaCl/10 mM sodium phosphate, pH 7.4/1 mM EDTA) at 60° C. for 30 min.

The packaging cell lines PA317, Miller et al., 1986, *Mol, Cell. Biol.* 6:2895–2902, GP+E-86, Markowitz et al., 1988, *J. Virol* 62:1120–1124, psiCRIP, Danos et al., 1988, *Proc. Natl. Acad. Sci. USA* 85:6460–6464, and their derivatives were maintained at 37° C. in Dulbecco's modified Eagle's medium (DMEM; GIBCO) with 10% (vol/vol) fetal bovine serum (CELLect Silver; Flow Laboratories) supplemented with 0.1 mM nonessential amino acids (Whittaker Bioproducts), antibiotics penicillin (5 units/ml), and streptomycin (5 µg/ml).

Improvement of the Viral Titer of the C4 Clone Since recent data indicated that supernatants containing high retroviral titers were the best candidates for transducing bone marrow cells, Bodine et al., 1990, *Proc. Natl. Acad Sci. USA* 87:3738–3742, the titer of the C4 producer clone was increased by "ping-pong" amplification, Bestwick et al., 1988, *Proc. Natl. Acad. Sci. USA* 85:5404–5408. Supernatant from nearly confluent C4 cultures was used to transduce GP+E-86 ecotropic packaging cells and G418 selection was applied. Forty-eight clones were isolated and screened by PEG precipitation for production of viral particles. Supernatants from 18 of these clones were DRB-positive by dot-blot analysis of viral RNA and had G418$^r$ titers between 0.5 and 3.5×10⁴ CFU/ml). One positive clone was then amplified by the ping-pong technique with the amphotropic hygromycin-resistant packaging line psiCRIP. Supernatants from 48 hygromycin-resistant clones were examined for presence of DRB-positive viral RNA by PEG precipitation and their G418$^r$ titers were determined. All of the clones were positive by dot-blot analysis with the DRB probes and produced titers between 1×10⁵ and 1×10⁷ CFU/ml. Amphotropic clone GS4.5 A4, which produced the highest titer, was tested for the presence of helper virus by the S+L-assay. No replication-competent helper virus was detected.

Amplification of virus titer was achieved by the ping-pong technique. Since there is evidence that psiCRIP packaging cells are less prone to produce helper virus than PA317 when using certain types of vectors, Miller, 1990, *Hum. Gene Therapy* 1:5–14, DRB recombinant virions were prepared using the psiCRIP/GP-E-86 producer combination. Titer values >1×10⁷ CFU/ml with no detectable amphotropic helper viruses were obtained, confirming that this strategy produced safe viral particles suitable for in vivo experiments.

Northern blot analysis of GS4.5-producing clones C4, A9, and A4, each derived from a different packaging cell line, showed a conserved hybridization pattern. RNA species corresponding to the full-length viral genome, the spliced Neo transcript, and the DRB transcription unit were observed with additional RNA species. High molecular size species observed in these experiments may constitute a read-through transcript starting from the TK promoter and ending in the other long terminal repeat (LTR). In contrast to many of the virion-producer clones obtained by transfection that presented erratic DRB transcripts, those obtained by transduction showed stable DRB hybridization patterns suggesting that no recombination events occurred during the amplification procedure.

Retroviral titers were determined as follows. Replication-defective retroviral particles were produced from packaging cell lines initially transfected with recombinant construct using the standard calcium phosphate precipitation method, Wigler et al., 1978, Cell 14:725–733. Retrovirus production was estimated by the drug-resistance titer (G418-resistant colony-forming units/ml, CFU/ml) as described, Bodine et al., 1990, Proc. Natl. Acad. Sci. USA 87:3738–3742. Except for the psiCRIP line, G418 (GIBCO) selection was carried out in active component at 500 µg/ml for 10–12 days. Hygromycin B selection was applied to psiCRIP-derived packaging clones in medium containing active drug at 50 µg/ml for 10 days. Replication-competent helper virus titer was assayed on PG4 feline cells by the $S^+L^-$ method, Bassen et al., 1971, Nature 229:564–566.

PEG precipitation of viral particles was performed as follows. Virions contained in 1 ml of culture supernatant were precipitated with 0.5 ml of 30% (wt/vol) polyethylene glycol (PEG) for 30 min. at 4° C. After centrifugation, the pellets were treated with a mixture of RNase inhibitors (vanadyl ribonuclease complex, BRL), phenol/chloroform-extracted, and ethanol-precipitated. Pellets were then resuspended in 15.7% (vol/vol) formaldehyde and serial dilutions were dotted onto nitrocellulose membrane.

Figure 2:
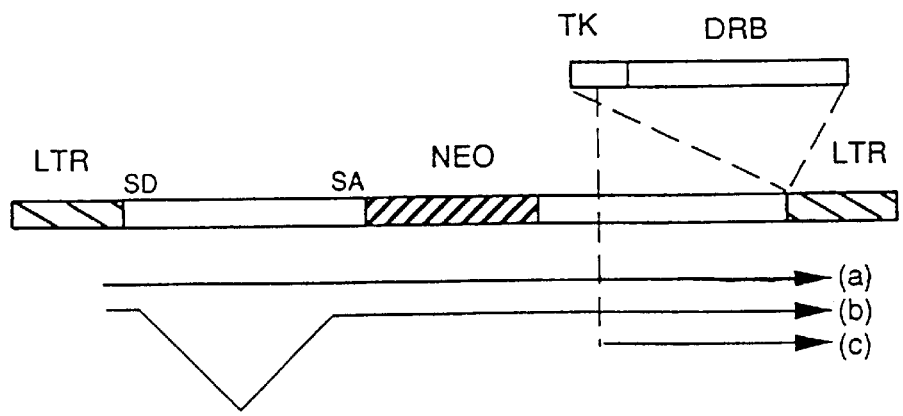
FIG. 2 is a diagram of the GS4.5 proviral genome and the expected transcripts.

Analysis of DRB Transcription in Packaging Cell Clones To test for accurate transcription of the introduced DRB cDNA within the different producer clones, Northern blots containing RNAs isolated from these clones were hybridized with the DRB and Neo probes. FIG. 2 depicts the structure of the provirus genome and the expected sizes of transcripts initiated from either the viral LTR or the TK promoters. Each of the three GS4.5-containing clones, which were derived from PA317 (clone C4), GP+E-86 (clone A9), and psiCRIP (clone A4) cells, showed DRB-positive transcripts. As reported, Hantzopoulos et al., 1989, Proc. Natl. Acad. Sci. USA 86:3519–3523, the unspliced genomic RNA (band a) and the spliced Neo transcript (band b) were observed. In addition a transcript uniquely hybridizable with the DRB probe was detected that corresponds to the size predicted (1700 bases, band c) for the DRB cDNA transcription unit.

Figure 3A:
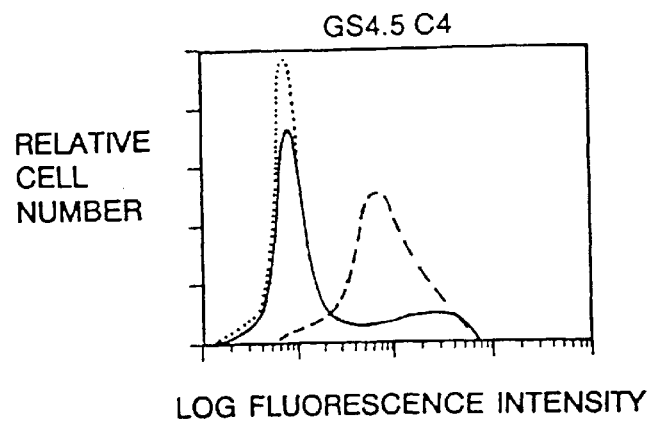
FIGS. 3a and 3b are representations of flow cytometry profile of transduced cells.
Figure 3B:
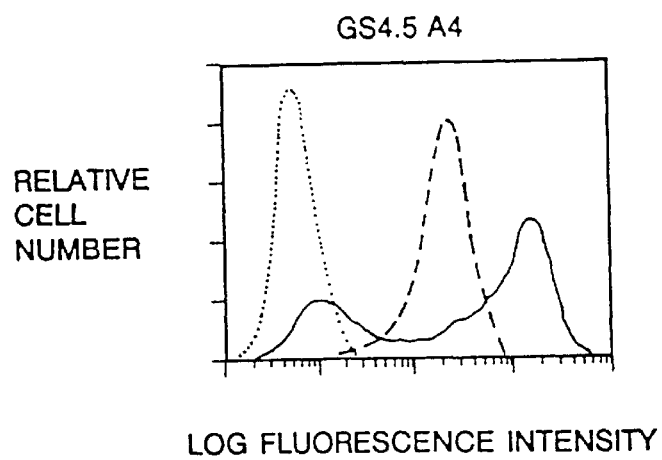

Surface Expression of the SLA-DR Antigen on Transduced Fibroblasts An in vitro assay was developed to examine surface expression of the SLA-DR antigen on murine fibroblasts. Flow cytometry (FCM) profiles shown in FIG. 3 demonstrate that $G418^r$ titers of $3\times10^4$ (clone C4) were sufficient to promote expression of the DR antigen on the cell surface of transduced DRA transfectants. In FIG. 3 solid lines indicate DR cell surface expression (anti-DR antibody binding) (22% and 75% of the bulk population of cells 3 days after transduction with GS4.5 C4, (B) and GS4.5 A4 (C), respectively); dashed lines indicate anti-mouse class I antibody binding (positive control); dotted lines indicate anti-pig CD8 antibody binding (negative control). Twenty-two percent of the bulk population of transduced cells were DR-positive and subclones maintained class II expression for more than 5 months. The increase in titer (clone A4) correlated with an increase in the number of cells transduced (75% of the transduced population was DR-positive) and with the brightness of the DR signal.

Figure 4:
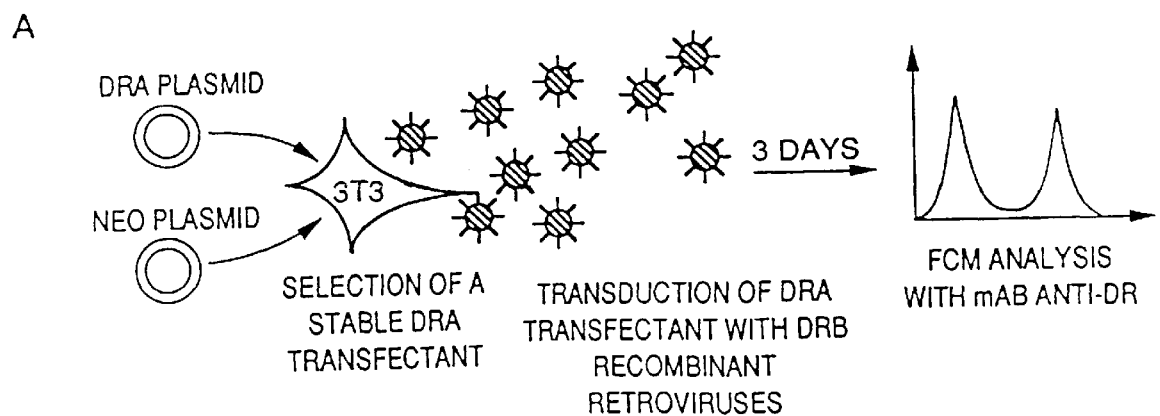
FIG. 4 is a diagram of the transduction assay.

The class II transduction assay was performed as diagrammed in FIG. 4. NIH 3T3 cells were transfected with the SLA-DRA$^d$ cDNA inserted in a plasmid expression vector, Okayama et al., 1982, Mol. Cell. Biol. 2:161–170. Approximately $3\times10^4$ cells of a stable DRA transfectant (clone 11/12.2F) that expressed a high level of DRA mRNA were then transduced overnight with 1 ml of DRB-containing retroviral supernatant. Cells were subsequently cultivated in fresh DMEM supplemented with 10% fetal bovine serum and antibiotics for 2 additional days and examined for cell surface expression of the DR antigen by FCM analysis.

The class II transduction assay described here provides a fast and simple method to test both the expression and functional titer of retroviral constructs. By using cells transfected with DRA, the need for lengthy double selection after transduction by two separated vectors, Yang et al., 1987, Mol. Cell Biol. 1:3923–3928; Korman et al., 1987, Proc. Natl. Acad. Sci. USA 84:2150–2154, is obviated. Cell-surface expression of DR heterodimers was demonstrated by FCM analysis 3 days after transduction, providing direct evidence that the transferred sequences were sufficient to produce significant level of DR β chain. More importantly, this test allows determination of "functional" titers based on the expression of the gene of interest rather than on that of the independently regulated drug-resistance marker.

The SLA-DRB probe was an EcoRi cDNA fragment containing the complete coding sequence of the DR β chain, Gustafsson et al., 1990, Proc. Natl. Acad. Sci. USA 87:9798–9802. The neomycin phosphotransferase gene (Neo) probe was the Bcl I-Xho I fragment of the N2A retroviral plasmid, Hantzopoulos et al., 1989, Proc. Natl. Acad. Sci. USA 86:3519–3523.

Expression of Porcine DRB cDNA Transduced into Murine Bone Marrow Progenitor Cells The efficiency with which myeloid clonogenic precursors were transduced was determined by assaying for CFU-GM with and without a selecting amount of G418 after exposure of bone marrow cells to GS4.5-derived virions. Comparison of the number of colonies that formed in the presence and absence of the drug, for two experiments, indicated that ≈40% of the initial population of myeloid progenitor cells were transduced. The frequency of $G418^r$ CFU-GM was again determined after a sample of the transduced marrow was expanded under long-term culture conditions for 33 days. Twenty-five percent of the progenitors present after 33 days in culture still gave rise to colonies under G418 selection. Colonies of cells arisen from CFU-GM were examined for the presence of DRB-specific transcripts by converting RNA into cDNA and then performing PCR amplification as described herein and in Shafer et al., 1991 Proc. Natl. Acad. Sci. USA 88:9670. A 360-bp DRB-specific product was detected in five of six G418-selected colonies from freshly transduced marrow, whereas all six colonies similarly derived from transduced progenitors present after 33 days in culture were positive. An additional band of 100 bp observed in some of the samples probably reflects the stoichastic nature of nonspecific priming events. DRB-specific transcripts were also detected in the bulk population of drug-resistant colonies and in producer cells but were not detected in controls such as a bulk population of untransduced colonies, fibroblasts used to provide carrier RNA, and a bulk population of transduced colonies processed as above but without reverse transcriptase. These latter data demonstrate that the PCR signal was dependent on the synthesis of cDNA, excluding the possibility that provirus, rather than viral message, was responsible for the amplified fragment.

Recent improvements including modifications of the virus design, increase of viral titers, use of growth factors to stimulate precursor cells, and selection of stem cells prior to transduction have been shown to improve long-term expression of transduced genes in the hematopoietic compartment, Bodine et al., 1990, *Proc. Natl. Acad. Sci. USA* 87:3738–3742; Bodine et al., 1989, *Proc. Natl. Acad. Sci. USA* 86:8897–8901; Wilson et al., 1990, *Proc. Natl. Acad. Sci. USA* 87:439–443; Kang et al., 1990, *Proc. Natl. Acad. Sci. USA* 87:9803–9807; Bender et al., 1989, *Mol. Cell. Biol.* 9:1426–1434. The experiments herein show the applicability of the retroviral gene-transfer technique in achieving expression of major histocompatibility complex class II genes transferred into hematopoietic cells. To determine the efficiency with which developmentally primitive hematopoietic cells were transduced, the frequency of $G418^r$ CFU-GM was assessed after expanding infected marrow cells kept for 33 days in long-term cultures. Expression of the exogenous DRB cDNA was also monitored in cells derived from transduced CFU-GM present either immediately after infection or after an extended culture period. Virtually all of the colonies individually tested were positive for DRB-specific transcript, suggesting that the DRB recombinant vector is suitable for expression in murine hematopoietic cells.

Bone marrow cells were obtained from the femora of 6- to 12-week-old female C57BL/10 mice and were prepared as described, Ildstad et al., 1984, *Nature* 307:168–170. Methylcellulose colony assays for granulocyte/macrophage colony-forming units (CFU-GM), Eaves et al., 1978, *Blood* 52:1196–1210, were performed as described using 5% (vol/vol) murine interleukin 3 culture supplement (Collaborative Research). Long-term Dexter-type bone marrow cultures were initiated in 60-mm culture dishes with $2\times10^7$ nucleated cells, Eaves et al., 1987, *CRC Crit. Rev. Oncol. Hernatol.* 7:125–138.

Bone marrow cells were transduced essentially as described, Bodine et al., 1989, *Proc. Natl. Acad. Sci. USA* 86:8897–8901. Briefly, bone marrow was harvested for 6–12-week-old female C57BL/I0 donors that had been treated 2 days with 5-fluorouracil (150 mg/kg). Prestimulation was performed by incubating $1\times10^6$ cells per ml for 2 days in long-term Dexter-type bone marrow culture medium to which was added 7.5% interleukin 3 culture supplement and recombinant human interleukin 6 (200 units/ml; gift from J. Jule, National Institutes of Health, Bethesda, Md.). Marrow cells were transduced for 48 hr by adding $5\times10^6$ cells per 10-cm plate containing nearly confluent virus-producers, Polybrene (8 mg/ml), and the cytokines described above.

Detection of DRB-Specific Transcripts in CFU-Derived Colonies was performed as follows. Cells corresponding to individual CFU colonies and to colonies present on an entire plate (bulk) were first extracted from methylcellulose cultures by dilution in phosphate-buffered saline and centrifugation. These cells were then combined with $1\times10^6$ NIH 3T3 cells (to provide carrier RNA), and total RNA was prepared using the guanidine isothiocyanate/CsCl method. First-strand cDNA was prepared from 20 µg of total RNA using the Invitrogen Red Module kit. cDNA was then subjected to 50 cycles of PCR amplification in the presence of the SLA DRB-specific oligonucieotides 04 (5'-CCACAGGCCTGATCCCTAATGG) (Seq. I.D. No. 1) and 17 (5'-AGCATAGCAGGAGCCTTCTCATG) (Seq. I.D. No. 2) using the Cetus GeneAmp kit as recommended (Perkin-Elmer/Cetus). Reaction products were visualized after electrophoresis on a 3% NuSieve agarose gel (FMC) by staining with ethidium bromide.

FCM analysis was performed with a FAC-Scan II fluorescence-activated cell sorter (Becton Dickenson) on cells stained with the anti-DR monoclonal antibody 40D, Pierres et al., 1980, *Eur. J. Immunol.* 10:950–957, an anti-$H-2^d$ allo antiserum, or the anti-porcine CD8 monoclonal antibody 76-2-11, Pescovitz et al., 1984, *J. Exp. Med.* 160:1495–1505, followed by fluorescein isothiocyanate-labeled goat anti-mouse antibodies (Boehringer Mannheim).

Expression of allogeneic class II cDNA in Swine Bone Barrow Cells Transduced With A Recombinant Retrovirus A MHC gene (DRB) was transferred into clonogenic progenitor cells from swine using a recombinant retroviral vector (GS4.5) and a transduction protocol designed to be applicable in vivo. Both the selectable drug resistance gene and the allogeneic class II cDNA transferred by this vector were expressed in the progeny of these transduced progenitors. Expression of the Neo gene was monitored functionally by colony formation under G418 selection, while the presence of class II transcripts was detected by PCR analysis. With this latter method, the transcriptional expression of both endogenous and virally derived DRB genes in transduced and selected colonies were demonstrated.

Primary porcine fibroblasts were cultured with high titer viral supernatants, and then analyzed by northern blotting using probes specific for DRB and Neo. A specific transcript was observed which was uniquely hybridizable with the DRB probe and migrated at the position predicted (1700 bases) for the DRB cDNA transcription unit arising from the TK promoter and terminating at the LTR 3' RNA processing site.

To determine whether GS4.5 containing virions could transduce swine myelopoietic progenitor cells a colony assay adapted for swine CFU-GM was used. Transductions were carried out by incubating bone marrow from a donor of the SLAC haplotype in high titer viral supernatant. Comparisons of the number of colonies which formed in the presence and absence of G418 for a total of 5 independent experiments indicated that 5% to 14% of CFU-GM were transduced.

Colonies of cells originating from transduced CFU-GM were examined for the presence of DRB-specific transcripts by converting RNA into cDNA, and then performing PCR amplification. Utilizing a polymorphic Sau3AI restriction site absent from the endogenous $DRB^c$ gene, the presence of $DRB^d$-specific transcripts was unambiguously demonstrated. Gel electrophoresis of the PCR product demonstrated that a 183/177 bp doublet indicative of the vector-derived $DRB^d$ transcript was amplified in samples derived not only from pools of transduced and selected CFU-GM progeny, but also from at least 4 out of 6 individual colonies tested. A 360 bp PCR fragment, indicative of endogenous $DRB^c$ transcripts, was also amplified not only as expected from PBL isolated from an SLAC donor, but also from both of the pooled colony samples and a number of the individual colony samples.

Construction of the retrovirus GS4.5, and production of high titer viral supernatants was as described above. Detection of DRB-specific transcripts in CFU-derived colonies by PCR of cDNA were described above and as follows. Bone marrow from an $SLA^c$ donor was exposed to GS4.5-containing virions, and G418 selected colonies were tested for the presence of $DRB^c$ (endogenous) and $DRB^d$ (vector derived) specific transcripts by PCR of cDNA followed by digestion with Sau3AI and agarose gel electrophoresis. Controls were as follows: template synthesized either in the presence or absence of reverse transcriptase; template derived from cells producing GS4.5-containing virions, from PBL isolated from $SLA^c$ or $SLA^d$ donors, and from untransduced producer cells used as carrier RNA.

Transduction of bone marrow was performed as follows. Swine bone marrow was harvested as previously described (Pennington et al., 1988, *Transplantation* 45:21–26) and transductions were carried out by incubating marrow cells in high titer viral supernatants at an m.o.i. of 3–5 in the presence of 8 ug of polybrene per ml at 37° C. for 5 hr. Myeloid progenitors were assayed by colony formation in methylcellulose cultures using PHA-stimulated swine lymphocyte conditioned medium as a source of growth factors. Selective medium contained 1.2 mg/ml active G418.

Transduced bone marrow was administered to a lethally irradiated miniature swine. At 5 weeks peripheral blood lymphocytes were analyzed by Southern, northern, and cell-surface FACS analyses. By all of these test there was evidence of presence of the transduced allogeneic class II gene in these cells and for expression of the product of this gene. In particular, northern analysis showed bands characteristic of the transcribed cDNA, and FACS analysis with a combination of alloantisera and monoclonal antibodies to DR showed presence of the transduced allele of DR beta on the surface of peripheral lymphocytes.

Allogenic Tolerance

Development of the B10.MBR-B10.AKM Strain Combination In an attempt to maintain strains which are truly congenic for the MHC, a program of continuous backcrossing of each congenic line to a common background partner strain was instituted more than 15 years ago. Backcross animals were intercrossed and appropriate progeny selected by serologic typing in order to reestablish each congenic line. Thus, C57BL/10 was used as one reference background strain and all other congenic lines on the B10 background were backcrossed once every six to ten generations to this C57BL/10 line.

Figure 5:
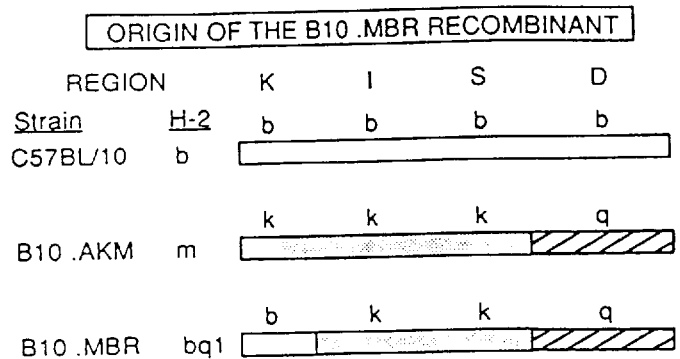
FIG. 5 is a diagram of genetic maps of the C57BL/10, B10.AKM, and B10.MBR strains.
Figure 6:
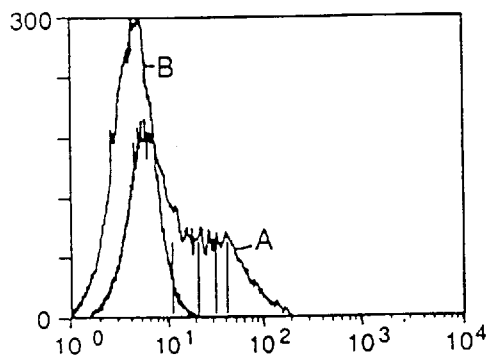
FIG. 6 is a diagram of the FACS profile of spleen cells from a recipient of transduced bone marrow.

During the backcrossing of each congenic line to its pedigreed reference line, there is of course the chance for an intra-MHC recombination event to occur. Typing of the intercross (F2) generation serologically reveals such recombinant events, and when the recombinant provides a new haplotype of potential interest for genetic studies, it is outcrossed and then intercrossed to produce a homozygous new recombinant H-2 haplotype. One of the most valuable of such recombinants originating in this colony is the B10.MBR line, Sachs et al., 1979, *J. Immunol.* 123:1965–1969, which was derived from a recombination event during the backcrossing of B10.AKM to C57BL/10. Because this strain was the first to separate $K^b$ from $I^k$ it has been used extensively in studies of R-2 immunogenetics. In addition, in combination with the parental B10.AKM strain, the B10.MBR offers the possibility of examining an isolated K gene as the only MHC difference between these two strains. Thus, as illustrated in FIG. 5, introduction of the $K^b$ gene into B10.AKM bone marrow stem cells, could theoretically lead to expression of all cell surface MHC antigens of the B10.MBR. Expression on bone marrow derived cell populations produces transplantation tolerance to the product of the transduced gene, and this tolerance can be tested by a tissue graft from the B10.MBR strain. Reconstitution of Myeloablated Mice with Transduced Bone Marrow Eighty prospective donor B10.AKM mice were treated with 150 mg/kg 5FU on day −7. Bone marrow was harvested from these mice on day −5, treated with anti-CD4 and anti-CD8 monoclonal antibodies (mAbs) plus complement to remove mature T cells, and cultured for five days with N2-B19-H2b virus-containing supernatant (H2) from the psi-Crip packaging cell line. As a control, one-half of the marrow was cultivated with supernatant from control packaging cells not containing N2-B19-H2b (A2). On day zero, 45 B10.AKM recipients received 10 Gy total body irradiation (TBI), followed by administration of various concentrations of cultured bone marrow cells (A2 or H2). $K^b$ expression On day 13 several animals receiving the lowest doses of cultured bone marrow were sacrificed and individual spleen colonies were harvested and analyzed by PCR for the presence of N2-B19-H2b DNA. In addition, spleen cell suspensions were prepared and analyzed for cell surface expression of $K^b$ by flow microfluorometry on a fluorescence-activated cell sorter (FACS). FACS analyses indicated that all animals receiving the H2-treated marrow showed some Level of $K^b$ expression above control staining with the non-reactive antibody. The results are shown in FIG. 6 which is a FACS profile of spleen cells from a recipient of transduced bone marrow: A=Anti $K^b$ antibody; B=control antibody. Spleen cells from recipients of non-transduced marrow were also negative. In addition, the PCR analysis showed every colony examined to contain the transduced DNA. Animals were thereafter followed by FACS and PCR on peripheral blood lymphocytes (PBL). On day 28 and again on day 40, PCR analyses were positive. However, FACS analysis for cell-surface expression was variable, with PBL from most H2 animals showing only a slight shift of the entire peak for staining with anti-$K^b$, as compared to PBL from A2 animals stained with the same antibody, or as compared to PBL from H2 animals stained with the non-reactive HOPC antibody.

Figure 7A:
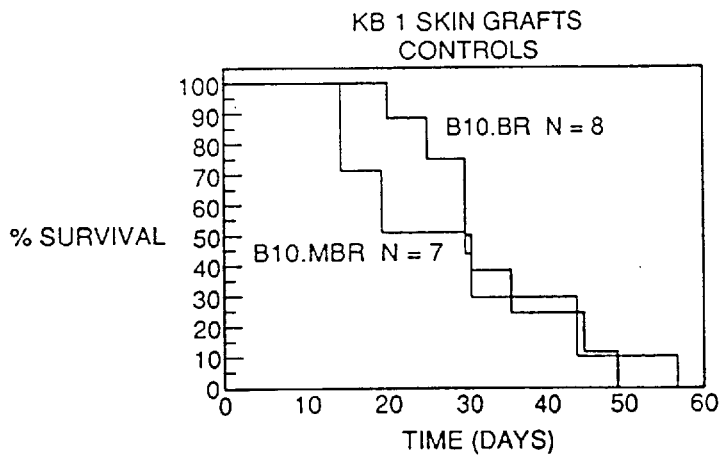
FIGS. 7a and 7b are graphs of survival versus time in skin graft experiments.
Figure 7B:
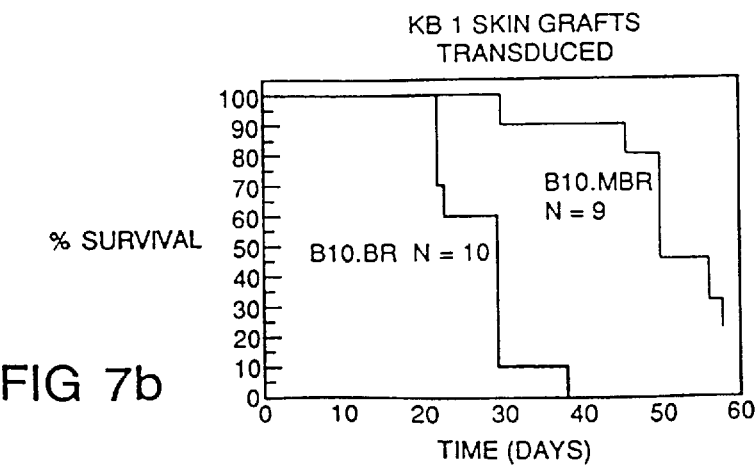
Figure 8A:
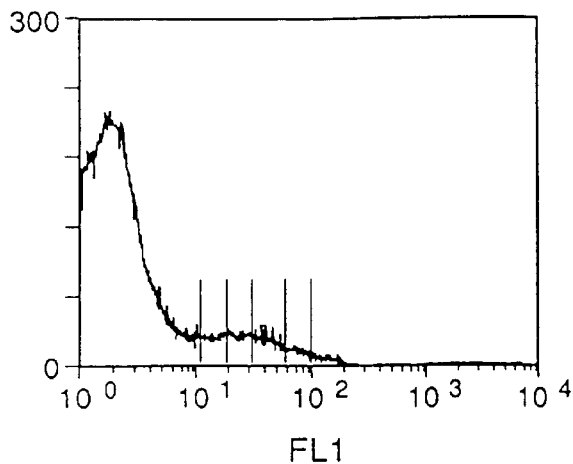
Figure 8B:
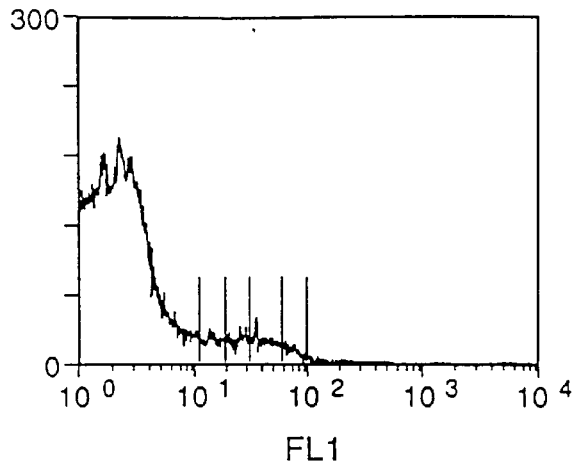
Figure 8C:
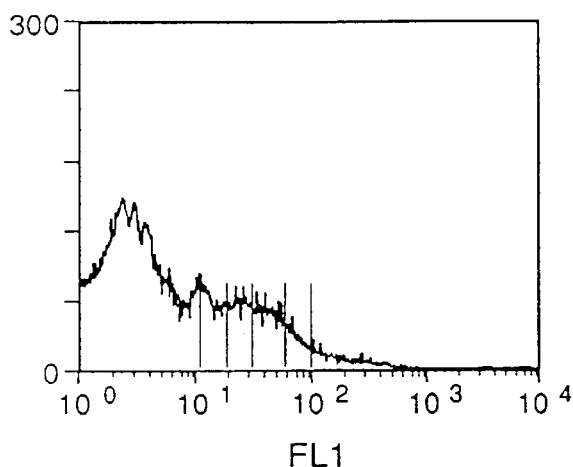
Figure 8D:
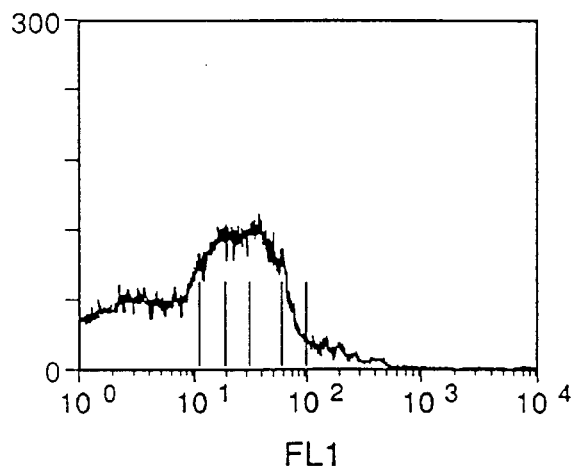

Allogeneic grafts On day 40 skin from B10.MBR ($K^b$ specific) and B10.BR (control, third party class I disparate) donors was grafted onto all animals. Graft survivals were scored daily by a blinded observer (i.e., readings were made without knowledge of which graft was from which donor strain) until rejection was complete. The survival times are shown in FIG. 7, and indicate marked specific prolongation of survival of the B10.MBR skin grafts on the recipients of $K^b$-transduced BMC (FIG. 7B), but not on recipients of control marrow (FIG. 7A). One of the animals with a long-standing intact B10.MBR skin graft was sacrificed at day 114 and cell suspensions of its lymphoid tissues were examined by FACS and compared to similar suspensions of cells from an animal which had rejected its B10.MBR skin graft. A striking difference was noted in staining of thymus cells with an anti-$K^b$ mAb. Cell suspensions were prepared and stained either with the anti-$K^b$ mAB 28-8-6 or the control antibody HOPC1. A subpopulation of thymus cells from the tolerant animal showed a marked shift toward increased staining with 28-8-6 compared to HOPC1, while there was essentially no change in the staining pattern of thymocytes from the animal which had lost its graft. FIG. 8 shows FACS analysis on thymocytes from skin graft rejector (FIG. 8A, B) and skin graft acceptor (FIG. 8C, D). Staining with control HOPC1 antibody (FIG. 8A, C) and with specific anti-$K^b$ antibody (FIG. 8B, D). A similar comparison of staining patterns on bone marrow cells showed the presence of low level $K^b$ expression on a cell population in the marrow of the tolerant mouse, but not of the mouse which had rejected its skin graft. These results indicate that a pluripotent stem cell or early progenitor cell population expressed $K^b$ in the tolerant mouse but not in the rejector mouse, and that this BMC stem cell provided a continuous source of $K^b$ antigen in the thymus on cells which are critical for the inactivation of developing thymocytes with $K^b$-reactive TCR. It is of interest to note that $K^b$ expression was not detected on splenocytes of the tolerant mouse, and that, in general, splenocyte expression did not correlate with skin graft tolerance. Since the spleen contains T cells which mature in the thymus, these results suggest that either thymocytes lose expression of $K^b$ as they mature, or that the $K^b$-bearing thymocytes of this animal were cells of a nonlymphoid lineage, such as macrophages. Long-term expression As discussed above, the B10.AKM and B10.MBR congenic mouse strains are identical except in the MHC class I region. A recombinant retrovirus containing the class I gene from the B10.MBR stain (H-2K$^b$) linked to a B19 parvovirus promoter (B19-H2K$^b$) and a neomycin resistance (neo$^r$) gene was introduced into B10.AKM (H-2K$^k$) marrow cells. As a control, a recombinant retrovirus containing only the neo$^r$ gene was introduced into B10.AKM marrow cells. The transduced marrow was injected into lethally irradiated AKM recipients pre-treated with an anti-CD8 monoclonal antibody. Twelve weeks post BMT, quantitative PCR was used to show that the B19-H-2K$^b$ proviral sequences were present in 5%–30% of peripheral blood cells in all recipient animals. Reverse transcriptase PCR was used to demonstrate the B19-H-2K$^b$ mRNA in RNA isolated from bone marrow and spleen of a subset of recipient animals.

Construction of the K$^b$ Retroviral Vector The retroviral vectors used the Maloney murine leukemia virus based vector N2, Armentano et al., 1987, *J. Virol.* 61:1647–1650. The coding regions within this virus were deleted during its construction, and replaced with the selectable marker gene, neomycin phosphotransferase (Neo), which is transcribed from the viral LTR promoter, and provides drug resistance to G418. This conventional N2 virus was then further modified by insertion of a parvovirus-derived promoter, B19, Liu et al., 1991, *J. Virol.* (In Press), downstream from Neo, followed by 1.6 kb of cDNA coding for the class I antigen H-2K$^b$ to form the new recombinant virus N2-B19-H26. FIG. 9 depicts the N2-B19-H26 retroviral vector: P=PstI; X=XhoI; H=HinDIII; E=EcoRI; B=BamHI. This latter cDNA was derived by Waneck et al. during the construction of an H-2$^b$ cDNA library for their purposes, Waneck et al., 1987, *J. Exp. Med.* 165:1358–1370.

Viral producer cell lines were developed using the packaging cell lines for amphotropic (psi-Crip), Danos et al., 1988, *Proc. Natl. Acad. Sci.* 85:6460–6464, and ecotropic (psi-2), Sambrook et al., 1989, *Molecular cloning: A laboratory manual.* Cold Spring Harbor Laboratory Press, Cold Spring Harbor, viral production. These cell lines have been specially designed to produce structural viral proteins for the recombinant defective virus to be produced. Viral production was achieved by transfecting psi-Crip with N2-B19-H2b. Both amphotropic and ecotropic producer cell lines were then co-cultivated allowing multiple integration events and high expression [i.e. the "ping-pong" technique see Bestwick et al., 1988, *Proc. Nalt. Acad. Sci.* 85:5404–5408]. In this technique, co-cultivation overcomes viral antigen receptor blockage by endogenously secreted proteins since amphotropic and ecotropic viruses recognize different receptors. Ecotropic psi-2 viral producer clones were then selected which produced titers of G418 resistance on 3T3 cells of greater than 10$^7$ cfu/ml.

In order to ensure that K$^b$ was being expressed from the recombinant virus, transduced 3T3 cells were stained with a monoclonal antibody specific to this antigen and analyzed by flow microfluorometry. These experiments clearly demonstrated high level expression of virally derived K$^b$.

Animals and husbandry were as follows. The B10.BMR strain, [Sachs et al., 1979, *J. Immunol.* 123:1965–1969, was provided to the Jackson Laboratory, Bar Harbor, Me. about 6 years ago, and specific pathogen-free stock animals of this strain are now available from that source. Upon arrival in animals should be transferred to autoclaved microisolator cages containing autoclaved feed and autoclaved acidified drinking water. Sterile animal handling procedures which are effective in maintaining animals free of pathogens so that interpretable survival studies can be performed should be used.

Bone marrow transplantation was performed as follows. Techniques for bone marrow transplantation in mice are known to those skilled in the art, see e.g., Sykes et al., 1988, *J. Immunol.* 140:2903–2911. Briefly, recipient B10.AKM mice aged 12 to 16 weeks are lethally irradiated (1025R, 137Cs source, 110R/min) and reconstituted within 8 hours with 2.5×10$^6$ bone marrow cells, obtained from the tibiae and femora of sex-matched donors aged 6–14 weeks. Animals are housed in sterilized microisolator cages, and receive autoclaved food and autoclaved acidified drinking water. For these studies some modifications of this general technique are required, since the syngeneic bone marrow will have been transduced with an allogeneic gene, and since the bone marrow will come from 5FU-treated mice, which should have lower total cell counts but higher stem cell content than normal mice. The protocol is therefore as follows:

1. Donors will be treated with 5-Fluorouracil, 150 mg/kg i.v. on day -7 in order to induce pluripotent stem cells to cycle.

2. Marrow will be harvested from donors on day -5, and T cell depleted with mAbs and complement.

3. Marrow will than be cultured for 5 days in supernatant from an ecotropic packaging cell line (B17H2Kb-18) which produces a high titer of non-infectious retroviral particles containing the K$^b$ gene (see below). IL-3 and IL-6 will be added to the cultures.

4. On day 0, recipient B10.AKM mice will be lethally irradiated (10.25 Gy), and will be reconstituted with 2.5×10$^6$ BMC transduced with the K$^b$ gene. Control animals will be similarly treated, except that they will receive marrow exposed to supernatant from a similar ecotropic packaging line not exposed to a K$^b$-containing vector. The recipient may also be pre-treated with anti-CD8 monoclonal antibody.

Cellular and serological assays are performed as follows.

Anti-class I Cell-Mediated Lympholysis (CM) Assay: Spleens are removed from BMT recipients and normal mice, red cells are lysed using ACK buffer, and a single cell suspension is prepared. Cells are filtered through 100-mesh nylon, washed, and resuspended at 4×10$^6$/ml in complete medium consisting of RPMI 1640 with 10% fetal calf serum, 0.025 mM 2-mercapteothanol, .0I M Hepes buffer, .09 mM nonessential amino acids, 1 mM sodium pyruvate, 2 mM glutamine, 100U/ml penicillin and 100 ug/ml streptomycin. 90 µl of responder cells are added to Costar 96-well round-bottomed plates along with irradiated (30 Gy) stimulator splenocytes. Cultures are set up in two rows of 3 replicates each, and after 5 days of incubation in 6% CO$_2$ at 37° C., twofold serial dilutions are prepared from the second row of triplicates, so that cytolytic capacity can be examined at a total of 5 different responder:target ratios. 51 Cr-labelled 2-day concanavalin A-induced lymphoblasts are then added at 10$^4$ blasts per well and incubated for 4 hr at 37° C., 6% CO$_2$. Plates are harvested using the Titertek supernatant collection system (Skatron, Inc., Sterling, Va.) and $^{51}$Cr release is determined using an automated gamma counter. Cytolytic capacity is measured directly in the original cell culture plated, so that the measurement is based on the number of responders plated, rather than on the number of live cells present at the end of the 5-day incubation period. This methodology has been developed and used successfully in this laboratory for several years for analysis of spleen cell responses from individual animals [Sykes, M., et al., 1988 *J. Immunol.* 140:2903–2911]. Percent specific lysis is calculated using the formula:

% Specific Lysis =

$$\frac{\text{Experimental release} - \text{Spontaneous release} \times 100\%}{\text{Maximum release} - \text{Spontaneous release}} \times 100$$

Limiting dilution analyses: Responder and stimulator ($6 \times 10^5$, 30 Gy irradiated) cells are concultured for 7 days in complete medium containing 13% TCGF [lectin-inactivated con A supernatant obtained from BALB/c con A-Activated splenocytes) in 96-well plates. Wells containing $10^5$ (24 wells), $3 \times 10^4$ (24 wells), $10^4$ (30 wells), 3000 (30 wells), 1000 (30 wells), 300 (30 wells), and 100 (30 wells) responder cells are prepared. Three thousand $^{51}$Cr-labeled con A blasts are added to each well on day 7, and 4 hour $^{51}$Cr release is measured. Wells are considered positive if $^{51}$Cr release is 3 standard deviations greater than the mean $^{51}$Cr release in 24 wells containing stimulator cells only plus similar numbers of target cells. The Poisson distribution is used to determine the frequency of precursor CTL's which recognize each target, and statistical analysis is performed by the Chi square method of Taswell, Taswell, 1981, *J. Immunol.* 126:1614.

Flow microfluorometry: One-color and two-color flow cytometry will be performed, and percentages of cells expressing a particular phenotype will be determined from 2-color data, as previously described in detail Sykes, 1990, *J. Immunol.* 145:3209–3215. The Lysis II software program (Becton Dickinson) will be used for distinguishing granulocytes from lymphocytes by gating on the basis of forward angle and 90° light scatter. Cell sorting will be performed on a Coulter Epics Elite cell sorter. Cell suspensions for flow cytometry: PBL, BMC, thymocyte, splenocyte, and lymph node suspensions will be prepared as previously described, Sykes, M. et al., 1988, *J. Immunol.* 140:2903–2911; Sykes, M. 1990, *J. Immunol.* 145:3209–3215; Sharabi, Y. et al., 1990, *J. Exp. Med.* 172:195–202. Whole peripheral white blood cell suspensions (including granulocytes) will be prepared by centrifugation of heparinized blood for 2 minutes at 14,000 RPM in an Eppendorf centrifuge, followed by aspiration of the buffy coat layer. These cells will be transferred to a 15 ml. conical tube and washed. Red blood cells (RBC) contaminating the remaining pellet will be lysed by exposure for 5 seconds to 4.5 ml of distilled $H_2O$ followed by rescue with 0.5 ml of 10×PBS.

Cell staining: One-color and two-color staining will be performed as we have previously described, Sykes, M., 1990, *J. Immunol.* 145:3209–3215; Sykes et al., 1988, *J. Immunol.* 141: 2282–2288. Culture supernatant of rat anti-mouse RcτR mAB 2.4G2, Unkeless, J.C., 1979, *J. Exp. Med.* 150:580–596, will be used for blocking of non-specific staining due to FcτR binding, whenever only direct staining is used. The following mABs are used: biotinylated murine $K^b$-specific $IgG_{2a}$ mAB 28-8-6, Ozato et al., 1981, *J. Immunol.* 126:317–321, and control murine $IgG_{2a}$, mAB HOPC1 (with no known specific binding to murine antigens) are prepared by purification on a protein A-Sepharose column, and are biotinylated by standard procedures used in our laboratory; rat anti-MAC1 mAB M1/70, Springer et al, 1979, *Eur. J. Immunol.* 9:301, is used as culture supernatant, and will be stained by mouse anti-rat IgG-specific mAB MAR18.5; FITC-labelled rat-anti-mouse granulocyte antibody Gr1 is purchased from Zymed; FITC-labelled rat-anti-mouse Thy1.2 mAb will be purchased from Becton-Dickinson; FITC-labelled mouse-anti-human CD3 mAb Leu4 (Becton Dickenson) is used as a directly FITC labeled negative control antibody.

Thymic tissue immunofluorescence: The tissue is incubated in L15 medium for 24 hours to reduce background staining, and is then cut and embedded in O.C.T. compound for freezing in Isopentane. Frozen sections are prepared (thickness 4 µm) on a cryostat, dried, fixed in acetone, then washed in PBS. The first antibody incubation (with 28-8-6) is performed in the presence of 2% normal mouse serum, in order to saturate Fc receptors. After 45 minutes, the slides are washed 4 times, and FITC-conjugated secondary reagent (monoclonal rat-anti-mouse IgG2a-FITC, purchased from Pandex) is added. After 45 minutes' incubation with the secondary reagent, four washes are performed and the tissue is mounted. Sections are examined under a fluorescence microscope by an observer who is unaware of the group of animals from which the tissue was obtained.

Bone Marrow Manipulations and Assays were performed as follows:

Transduction of murine bone marrow stem cells: The methodology used for transduction of bone marrow cells has been described previously, Karlsson et al., 1988, *Proc. Natl. Acad. Sci.* 85:6062–6066. Bone marrow is harvested from 6–12 week old female B10.AKM donors treated 2 days previously with 150 mg/kg 5-FU. Following T cell depletion (see above), the marrow is divided and $10^7$ cells per 10 cm plate are cultured for 5 days in the presence of 8 µg of Polybrene per ml, 10% FCS, 0.6% IL-3-containing supernatant, 0.6% IL-6-containing supernatant, and fresh supernatants from $B19H2K^b$ or N2 cells. IL-3- and IL-6-containing supernatant is 48 hour supernatant of COS 7 cells transfected with the murine rIL-3 gene-containing plasmid pCD-IL-3 or with the murine rIL-6 gene-containing plasmid pCD-IL-6, respectively (both plasmids provided by Dr. Frank Lee, DNAX Corp.). IL-3-containing supernatants are tittered by testing proliferation of the IL-3-dependent cell line 32D in the presence of dilutions of these supernatants, and IL-6 is tittered in a similar manner using the IL-6-dependent line T1165 as the indicator cell line. We will also test the effect of murine SCF on bone marrow transduction, as recently described, Zsebo et al., 1990, *Cell* 63:125–201.

The virus-containing supernatants are refreshed on a daily basis by harvesting the non-adherent layer of each plate, pelleting the cells, and resuspending in freshly harvested filtered virus-containing $B19H2K^b$ or N2 supernatant with additives. After 5 days, the non-adherent and adherent BMC are harvested, washed, and resuspended at $2.5 \times 10^6$/ml in Medium 199 with Hepes buffer and Gentamycin plus Heparin 10 U/Ml. One ml. of this suspension is injected i.v. to irradiated mice.

Murine CFU-GM assay: To test for the bone marrow progenitor cells known as CFU-GM (colony forming unit-granulocyte/macrophage), bone marrow cells are suspended in plating medium consisting of IMDM medium containing 30% defined fetal bovine serum (FBS) (HyClone, Logan, Utah), $10^{-4}$M β-mercaptoethanol, antibiotics, 5% v/v murine IL-3 culture supplement (Collaborative Research Inc., Bedford, Mass.) and 0.8% methylcellulose (achieved by adding 36% v/v of a commercially prepared solution purchased from the Terry Fox Laboratory, Vancouver). 1.1 ml of this suspension is then dispensed into 35mm tissue culture plates (in duplicate), and placed in a 37° C. incubator. The resulting CFU-GM derived colonies are enumerated microscopically after 5–7 days. Transduced CFU-GM are selected by including 0.9 ug/ml active G418 in the culture medium. The transduction frequency is then determined by the ratio of CFU-GM which form colonies in the presence and in the absence of the drug.

Molecular methods were as follows:

Construction of N2-B19-H2b vector: This vector was constructed staring from the original retroviral vector N2, Eglitis et al., 1985, *Science* 230:1395–1398, as modified by Shimada to include an additional BamHI site immediately 3' of the XhoI site. It includes the $K^b$ cDNA previously cloned in the vector pBG367, as described by G. Waneck, Waneck et al., 1987, *J. Exp. Med.* 165:1358–1370. This gene has been placed under control of the B19 promoter, a highly efficient parvo virus derived promoter, Liu et al., 1991, *J. Virol. In Press*:] to produce the N2-B19-H2b construct.

Southern blot analysis can be performed on DNA extracted from PBL, thymocyte, BMC, splenocyte or lymph node cell suspensions using standard methods, Ausubel et al., 1989, *Current protocols in molecular biology*. John Wiley & Sons, New York, and probing will be performed with the fragment of $K^b$ cDNA released from pBG367 by EcoRI. The genomic DNA will be cut with enzymes capable of distinguishing the transduced $K^b$ from other class I genes of the B10.AKM strain. From known sequences it would appear that EcoRI may be satisfactory for this purpose, since it should liberate a 1.6 kb band from the transduced $K^b$ cDNA, which is distinct from both the expected endogenous $K^k$ and $D^q$ class I bands of B10.AXM, Arnold et al., 1984, *Nucl. Acids Res.* 12:9473–9485, Lee et al., *J. Exp. Med.* 168:1719–1739. However, to assure that there is no confusion with bands liberated from other class I and class I-like genes we will test several enzymes first on DNA from B10.AKM and choose appropriate restriction enzyme combinations.

PCR analysis of DNA can be performed using primers previously shown to be effective in our preliminary studies (see FIG. 4):

5' primer: 5'-GGCCCACACTCGCTGAGGTA-TTTCGTC-3' (covers 5' end of α1 exon) (Seq. ID No.3)

3' primer: 5'-GCCAGAGATCACCTGAATAGTGTGA-3' (covers 5' end of α2 exon) (Seq. ID No. 4)

DNA is subjected to 25 cycles of PCR amplification using these specific oligonucleotides and the Cetus GeneAmp kit (Perkin Elmer Cetus, Norwalk, Conn.) according to the manufacturer's directions. In addition, $[^{32}P]dCTP$ will be included in the PCR reaction in order to visualize products by autoradiography following electrophoresis.

RNA can be isolated from $5\times10^6$ to $5\times10^7$ cells using the guanidine isothiocyanate and CsCl methods, Chirgwin et al., 1979, *Biochem.* 18:5294–5308, and will be used for northern analyses, RNase protection analyses, and for PCR analyses of products formed by reverse transcriptase. For situations in which less then $5\times10^6$ cells are available, for example following tail bleedings of individual mice, we will utilize the QuickPrep mRNA Purification Kit (Amgen) as miniaturized RNA preparation procedure.

Northern analyses can be carried out using standard methods, Ausubel et al., 1989, *Current protocols in molecular biology* John Wiley & Sons, New York, and the same $K^b$ cDNA-derived probe. Vector-derived $K^b$ mRNA is larger than endogenous class I transcripts (2.5 kb vs. 1.6 kb) due to the inclusion of vector sequences between the 3' end of the cDNA and the poly-adenylation site in the viral 3' LTR. It should therefore be easy to distinguish the vector-derive $K^b$ mRNA from endogenous transcripts that might cross-hybridize with a $K^b$ cDNA probe. We will also utilize probes derived from unique non-$K^b$ sequences of the transcript (e.g., from B19 or N2 derived vector sequences).

RNAse protection analyses are more sensitive than standard northern blots, yet still quantitative. Procedures based on published methods, Sambrook et al., 1989, *Molecular cloning: A laboratory manual*. Cold Spring Harbor Laboratory Press, Cold Spring Harbor, will be used to derive riboprobes. Briefly, the Kb cDNA will be cloned into a plasmid vector containing the T3 and T7 RNA polymerase promoter sequences (bluescript or Bluescribe plasmids from Stratagene). Using appropriate polymerase and $^{32}P$-nucleotides, transcription of the insert will be initiated and the radioactive $K^b$ RNA will be purified. This probe will then be incubated with various RNA preparations followed by treatment with ribonuclease. Presence of RNA will be assessed by electrophoresis on a sequencing gel.

PCR following reverse transcriptase treatment of RNA will be used as a highly sensitive procedure for detecting the $K^b$ transcript. Appropriate primers will be designed in order to specifically amplify retroviral derived transcripts (one primer covering the 5'UT region of the construct and second derived from the cDNA sequence). Briefly, RNA will be prepared by the GuSCN/CsCl method and first strand cDNA will be prepared from 5 ug of total RNA using the Super-Script preamplification system (BRL/Life Technologies, Inc., Gaithersburg, Md.). PCR amplifications will be conducted for 50 cycles, Hansen et al., *J. Immunol.*118:1403–1408, using the Cetus GeneAmp kit (Perkin Elmer Cetus, Norwalk, Conn.). Reaction products will be visualized following electrophoresis on a 3% NuSieve agarose gel (FMC BioProducts, Rockland, Me.).

Allogeneic MHC gene transfer plus cyclosporine

It has been shown previously in partially inbred miniature swine that differences in class II MHC loci are of critical importance in determining the fate of primarily vascularized allografts. Cyclosporine given early in the posttransplant period uniformly leads to tolerance of class II matched class I mismatched kidney allografts. However, cyclosporine alone does not produce tolerance across a full-MHC barrier. Consistent with the importance of class II allogeneic bone marrow transplantation across class II barriers induces tolerance to kidney transplants matched to the class II of the bone marrow donors, but completely disparate to the recipients. In the following experiment specific transplantation tolerance to complete SLA-disparate kidney transplant was induced with autologous bone marrow transplantation in which the recipient's marrow was genetically modified prior to transplant by transduction with a retroviral expression vector carrying an allogenic SLA class II gene. The retroviral expression vectors contained cDNA for either SLA-$DRB^a$ or -$DRB^c$ and a drug selection marker (Neo), and high tittered viral supernatants were prepared using amphotropic packaging cell lines. Bone marrow from five animals included in this study was harvested on day 2, and then cultured with virus-containing supernatant for either an allogeneic (n=4) or syngeneic (n=1) MHC gene for a approximately 48 hours. After lethal irradiation (10 Gy in two fractions 24 hours apart) in days −1 and 0, animals were transplanted with 0.4 to $1.3\times10^8$ cells/kg on day 0. The effectiveness of the gene transfer was tested using a colony forming unit assay for granulocyte/macrophage progenitors (CFU-GM) in the presence of G418 to select for neomycin resistance. The frequency of G418 resistant CFU-GM varied significantly between animals (6.5% to 25.9%) immediately after transduction and diminished slowly with time. All animals regained their responsiveness to allogeneic stimuli by the third month post-bone marrow transplantation, as tested by MLR. MAbs specific for DQ and DR molecules of the class II MHC were used for "blocking" MLR studies, to separate the effects of recognition of DQ and DR. In assays using cells from recipients of bone marrow transplantation transduced with the allogeneic DRB gene, the DR portion of the response to the gene-donor type cells was strongly diminished, demonstrating the effectiveness of the transduced gene at inducing DR-specific unresponsiveness. This effect was observed in all experimental animals, although more pronounced in the DRB$^d$ to cc combination than in DRB$^a$ to gg direction. In MRL using cells from a control animal transduced with a syngeneic gene, blocking of DR or DQ in MLR showed a pattern of reactivity identical to that observed in naive animals of the same haplotype. Five months after BMT, animals were challenged with kidney transplants matched for class II of the gene-donor type, and fully mismatched to the original recipient haplotype. Cyclosporine 10 to 15 mg/kg/day iv was given for 12 days, to tolerize for the class I MHC and minor antigen disparity. Three animals rejected their kidney transplants at days 8, 22 and 40. The accelerated manner of rejection at day 8 suggested sensitization as an undesirable effect of the expression of the allogeneic gene product. In none of these recipients could the presence of anti-donor type antibodies be detected by flow cytometry. One animal became tolerant and exhibited normal creatinine levels at 101 days posttransplant. The animal which received the bone marrow transduced with a syngeneic gene underwent severe rejection with high creatinine levels and vascular changes in pathology. The recipient of the longest surviving kidney transplant also received the most efficiently transduced autologous bone marrow, as judged on the initial frequency of G418r CFU-GM. In this one case, recombinant cytokines (Pixy 321 (Pixy is a human-GM-CSF/IL3 fusion protien) 100 Units/ml; mouse stem cell growth factor 20 Units/ml; although these cytokines were used, cytokines from the same species as the cell being transformed can also be used) were included in the culture medium during transduction with the allogeneic DRB retroviral expression vector. The cytokines may have led to the transduction of multilineage pluripotent hematopoietic stem cells, including the precursors of dendritic cells which ultimately induced DRB-specific hyporesponsiveness. These experiments demonstrate that somatic class II MHC DRB gene transfer into bone marrow cells has profound functional consequences upon the immune responses of the recipient. In vitro, and more importantly in vivo, immune function was significantly modulated, with the induction of donor specific prolongation of fully mismatched kidney transplant survival. The transduction of allogeneic bone marrow stem cells with MHC genes provides a method of inducing tolerance across MHC barriers by a mechanism comparable to lymphohematopoietic chimerism. The lethal irradiation used in the experiments described herein can be replaced with a non-myeloablative conditioning regime that would permit bone marrow engraftment in a more clinically acceptable fashion.

II. The induction of tolerance with bone marrow transplantation

A short course of high dose of cyclosporine (administered in absence of treatments, e.g., treatment with Prednisone, which stimulate cytokine release) to induce tolerance to class I and other minor disparities combined with implantation of bone marrow cells induce tolerance to class II disparity.

Xenografts: The following procedure was designed to lengthen the time an implanted organ (a xenograft) survives in a xenogeneic host prior to rejection. The organ can be any organ, e.g., a liver, e.g., a kidney, e.g., a heart. The main strategies are elimination of natural antibodies by organ perfusion, transplantation of tolerance-inducing bone marrow, optionally, the implantation of donor stromal tissue, and, optionally, the administration of a short course of a help reducing agent at about the time of introduction of the graft, as described above. preparation of the recipient for transplantation includes any or all of these steps. Preferably they are carried out in the following sequence.

First, a preparation of horse anti-human thymocyte globulin (ATG) is intravenously injected into the recipient. The antibody preparation eliminates mature T cells and natural killer cells. If not eliminated, mature T cells would promote rejection of both the bone marrow transplant and, after sensitization, the xenograft itself. Of equal importance, the ATG preparation also eliminates natural killer (NK) cells. NK cells probably have no effect on the implanted organ, but would act immediately to reject the newly introduced bone marrow. Anti-human ATG obtained from any mammalian host can also be used, e.g., ATG produced in pigs, although thus far preparations of pig ATG have been of lower titer than horse-derived ATG. ATG is superior to anti-NK monoclonal Antibodies, as the latter are generally not lytic to all host NK cells, while the polyclonal mixture in ATG is capable of lysing all host NK cells. Anti-NK monoclonal antibodies can, however, be used.

The presence of donor antigen in the host thymus during the time when host T cells are regenerating post-transplant is critical for tolerizing host T cells. If donor hematopoietic stem cells are not able to become established in the host thymus and induce tolerance before host T cells regenerate repeated doses of anti-recipient T cell antibodies may be necessary throughout the non-myeloablative regimen. Continuous depletion of host T cells may be required for several weeks. Alternatively, e.g. if this approach is not successful, and tolerance (as measured by donor skin graft acceptance, specific cellular hyporesponsiveness in vitro, and humoral tolerance) is not induced in these animals, the approach can be modified to include host thymectomy. In thymectomized recipients, host T cells do not have an opportunity to differentiate in a host thymus, but must differentiate in the donor thymus. If this is not possible, then the animal has to rely on donor T cells developing in the donor thymus for immunocompetence. Immunocompetence can be measured by the ability to reject a non-donor type allogeneic donor skin graft, and to survive in a pathogen-containing environment.

It may also be necessary or desirable to splenectomize the recipient in order to avoid anemia.

Second, the recipient is administered low dose radiation in order to make room for newly injected bone marrow cells. A sublethal dose of between 100 rads and 400 rads whole body radiation, plus 700 rads of local thymic radiation, has been found effective for this purpose.

Third, natural antibodies are absorbed from the recipient's blood by hemoperfusion of a liver of the donor species. Pre-formed natural antibodies (nAB) are the primary agents of graft rejection. Natural antibodies bind to xenogeneic endothelial cells and are primarily of the IgM class. These antibodies are independent of any known previous exposure to antigens of the xenogeneic donor. B cells that produce these natural antibodies tend to be T cell-independent, and are normally tolerized to self antigen by exposure to these antigens during development. The mechanism by which newly developing B cells are tolerized is unknown. The liver is a more effective absorber of natural antibodies than the kidney.

The fourth step in the non-myeloablative procedure is to implant donor stromal tissue, preferably obtained from fetal liver, thymus, and/or fetal spleen, into the recipient, preferably in the kidney capsule. Stem cell engraftment and hematopoiesis across disparate species barriers is enhanced by providing a hematopoietic stromal environment from the donor species. The stromal matrix supplies species-specific factors that are required for interactions between hematopoietic cells and their stromal environment, such as hematopoietic growth factors, adhesion molecules, and their ligands.

As liver is the major site of hematopoiesis in the fetus, fetal liver can also serve as an alternative to bone marrow as a source of hematopoietic stem cells. The thymus is the major site of T cell maturation. Each organ includes an organ specific stromal matrix that can support differentiation of the respective undifferentiated stem cells implanted into the host. Although adult thymus may be used, fetal tissue obtained sufficiently early in gestation is preferred because it is free from mature T lymphocytes which can cause GVHD. Fetal tissues also tend to survive better than adult tissues when transplanted. As an added precaution against GVHD, thymic stromal tissue can be irradiated prior to transplantation, e.g., irradiated at 1000 rads. As an alternative or an adjunct to implantation, fetal liver cells can be administered in fluid suspension.

Fifth, bone marrow cells (BMC), or another source of hematopoietic stem cells, e.g., a fetal liver suspension, of the donor are injected into the recipient. Donor BMC home to appropriate sites of the recipient and grow contiguously with remaining host cells and proliferate, forming a chimeric lymphohematopoietic population. By this process, newly forming B cells (and the antibodies they produce) are exposed to donor antigens, so that the transplant will be recognized as self. Tolerance to the donor is also observed at the T cell level in animals in which hematopoietic stem cell, e.g., BMC, engraftment has been achieved. When an organ graft is placed in such a recipient several months after bone marrow chimerism has been induced, natural antibody against the donor will have disappeared, and the graft should be accepted by both the humoral and the cellular arms of the immune system. This approach has the added advantage of permitting organ transplantation to be performed sufficiently long following transplant of hematopoietic cells, e.g., BMT, e.g., a fetal liver suspension, that normal health and immunocompetence will have been restored at the time of organ transplantation. The use of xenogeneic donors allows the possibility of using bone marrow cells and organs from the same animal, or from genetically matched animals.

Finally, a short course of a help reducing agent, e.g., a short course of high dose CsA is administered to the recipient. As is described above, the course is begun at about the time of implantation, or a little before, and is continued for a time about equal to the time it takes for a mature T cell to be stimulated and initiate rejection. While any of these procedures may aid the survival of an implanted organ, best results are achieved when all steps are used in combination. Methods of the invention can be used to confer tolerance to allogeneic grafts, e.g., wherein both the graft donor and the recipient are humans, and to xenogeneic grafts, e.g., wherein the graft donor is a nonhuman animal, e.g., a swine, e.g., a miniature swine, and the graft recipient is a primate, e.g., a human.

While any of these procedures may aid the survival of an implanted organ, best results are achieved when all steps are used in combination. Methods of the invention can be used to confer tolerance to allogeneic grafts, e.g., wherein both the graft donor and the recipient are humans, and to xenogeneic grafts, e.g., wherein the graft donor is a nonhuman animal, e.g., a swine, e.g., a miniature swine, and the graft recipient is a primate, e.g., a human.

In the case of xenogeneic grafts, the donor of the implant and the individual that supplies either the tolerance-inducing hematopoietic cells or the liver to be perfused should be the same individual or should be as closely related as possible. For example, it is preferable to derive implant tissue from a colony of donors that is highly inbred.

Detailed Protocol

In the following protocol for preparing a cynomolgus monkey for receipt of a kidney from a miniature swine donor, zero time is defined as the moment that the arterial and venous cannulas of the recipient are connected to the liver to be perfused.

On day −1 a commercial preparation (Upjohn) of horse anti-human anti-thymocyte globulin (ATG) is injected into the recipient. ATG eliminates mature T cells and natural killer cells that would otherwise cause rejection of the bone marrow cells used to induce tolerance. The recipient is anesthetized, an IV catheter is inserted into the recipient, and 6 ml of heparinized whole blood are removed before infection. The ATG preparation is then injected (50 mg/kg) intravenously. Six ml samples of heparinized whole blood are drawn for testing at time points of 30 min., 24 hours and 48 hours. Blood samples are analyzed for the effect of antibody treatment on natural killer cell activity (testing on K562 targets) and by FACS analysis for lymphocyte subpopulations, including CD4, CD8, CD3, CD11b, and CD 16. Preliminary data from both assays indicate that both groups of cells are eliminated by the administration of ATG. If mature T cells and NK cells are not eliminated, ATG can be re-administered at later times in the procedure, both before and after organ transplantation.

Sublethal irradiation is administered to the recipient between days −1 and −8. Irradiation is necessary to eliminate enough of the recipient's endogenous BMC to stimulate hematopoiesis of the newly introduced foreign BMC. Sublethal total body irradiation is sufficient to permit engraftment with minimal toxic effects to the recipient. Whole body radiation (150 Rads) was administered to cynomolgus monkey recipients from a bilateral (TRBC) cobalt teletherapy unit at 10 Rads/min. Local irradiation of the thymus (700 Rads) was also employed in order to facilitate engraftment.

Natural antibodies are a primary cause of organ rejection. To remove natural antibodies from the recipient's circulation prior to transplantation, on day 0 an operative absorption of natural antibodies (nAB) is performed, using a miniature swine liver, as follows. At −90 minutes the swine donor is anesthetized, And the liver prepared for removal by standard operative procedures. At −60 minutes the recipient monkey is anesthetized. A peripheral IV catheter is inserted, and a 6 ml sample of whole blood is drawn. Through mid-line incision, the abdominal aorta and the vena cava are isolated. Silastic cannulas containing side ports for blood sampling are inserted into the blood vessels.

At −30 minutes the liver is perfused in situ until it turns pale, and then removed from the swine donor and placed into cold Ringers Lactate. The liver is kept cold until just prior to reperfusion in the monkey. A liver biopsy is taken. At −10 minutes the liver is perfused with warm albumin solution until the liver is warm (37 degrees).

At 0 time the arterial and venous cannulas of the recipient are connected to the portal vein and vena cava of the donor liver and perfusion is begun. Liver biopsies are taken at 30 minutes and 60 minutes, respectively. Samples of recipient blood are also drawn for serum at 30 minutes and 60 minutes respectively. At 60 minutes the liver is disconnected from the cannulas and the recipient's large blood vessels are repaired. The liver, having served its function of absorbing harmful natural antibodies from the recipient monkey, is discarded. Additional blood samples for serum are drawn from the recipient at 2, 24, and 48 hours. When this procedure was performed on two sequential perfusions of swine livers, the second liver showed no evidence of mild ischemic changes during perfusion. At the end of a 30 minute perfusion the second liver looked grossly normal and appeared to be functioning, as evidenced by darkening of the venous outflow blood compared to the arterial inflow blood in the two adjacent cannulas. Tissue sections from the livers were normal, but immunofluorescent stains showed IgM on endothelial cells. Serum samples showed a decrease in natural antibodies.

To promote long-term survival of the implanted organ through T-cell and B-cell mediated tolerance, donor bone marrow cells are administered to the recipient to form chimeric bone marrow. The presence of donor antigens in the bone marrow allows newly developing B cells, and newly sensitized T cells, to recognize antigens of the donor as self, and thereby induces tolerance for the implanted organ from the donor. To stabilize the donor BMC, donor stromal tissue, in the form of tissue slices of fetal liver, thymus, and/or fetal spleen are transplanted under the kidney capsule of the recipient. Stromal tissue is preferably implanted simultaneously with, or prior to, administration of hematopoietic stem cells, e.g., BMC, or a fetal liver cell suspension.

To follow chimerism, two color flow cytometry can be used. This assay uses monoclonal antibodies to distinguish between donor class I major histocompatibility antigens and leukocyte common antigens versus recipient class I major histocompatibility antigens. BMC can in turn be injected either simultaneously with, or preceding, organ transplant. Bone marrow is harvested and injected intravenously ($7.5 \times 10^8$/kg) as previously described (Pennington et al., 1988, Transplantation 45:21–26). Should natural antibodies be found to recur before tolerance is induced, and should these antibodies cause damage to the graft, the protocol can be modified to permit sufficient time following BMT for humoral tolerance to be established prior to organ grafting.

The approaches described above are designed to synergistically prevent the problem of transplant rejection. When a kidney is implanted into a cynomolgus monkey following liver absorption of natural antibodies, without use of bone marrow transplantation to induce tolerance, renal functions continued for 1–2 days before rejection of the kidney. When four steps of the procedure were performed (absorption of natural antibodies by liver perfusion, administration of ATG, sublethal irradiation and bone marrow infusion, followed by implant of a porcine kidney into primate recipient), the kidney survived 7 days before rejection. Despite rejection of the transplanted organ, the recipient remained healthy.

When swine fetal liver and thymic stromal tissue were implanted under the kidney capsule of two sublethally irradiated SCID mice, 25–50% of peripheral blood leukocytes were of donor lineage two weeks post-transplantation. A significant degree of chimerism was not detected in a third animal receiving fetal liver without thymus.

The methods of the invention may be employed in combination, as described, or in part.

The method of introducing bone marrow cells may be altered, particularly by (1) increasing the time interval between injecting hematopoietic stem cells and implanting the graft; (2) increasing or decreasing the amount of hematopoietic stem cells injected; (3) varying the number of hematopoietic stem cell injections; (4) varying the method of delivery of hematopoietic stem cells; (5) varying the tissue source of hematopoietic stem cells, e.g., a fetal liver cell suspension may be used; or (6) varying the donor source of hematopoietic stem cells. Although hematopoietic stem cells derived from the graft donor are preferable, hematopoietic stem cells may be obtained from other individuals or species, or from genetically-engineered inbred donor strains, or from in vitro cell culture.

Methods of preparing the recipient for transplant of hematopoietic stem cells may be varied. For instance, recipient may undergo a splenectomy or a thymectomy. The latter would preferably be administered prior to the non-myeloablative regimen, e.g., at day −14.

Hemoperfusion of natural antibodies may: (1) make use of other vascular organs, e.g., liver, kidney, intestines; (2) make use of multiple sequential organs; (3) vary the length of time each organ is perfused; (4) vary the donor of the perfused organ. Irradiation of the recipient may make use of: (1) varying the absorbed dose of whole body radiation below the sublethal range; (2) targeting different body parts (e.g., thymus, spleen); (3) varying the rate of irradiation (e.g., 10 rads/min, 15 rads/min); or (4) varying the time interval between irradiation and transplant of hematopoietic stem cells; any time interval between 1 and 14 days can be used, and certain advantages may flow from use of a time interval of 4–7 days. Antibodies introduced prior to hematopoietic cell transplant may be varied by: (1) using monoclonal antibodies to T cell subsets or NK cells (e.g., anti-NKH1$_A$, as described by U.S. Pat. No. 4,772,552 to Hercend, et al., hereby incorporated by reference); (2) preparing anti-human ATG in other mammalian hosts (e.g., monkey, pig, rabbit, dog); or (3) using anti-monkey ATG prepared in any of the above mentioned hosts.

The methods of the invention may be employed with other mammalian recipients (e.g., rhesus monkeys) and may use other mammalian donors (e.g., primates, sheep, or dogs). As an alternative or adjunct to hemoperfusion, host antibodies can be depleted by administration of an excess of hematopoietic cells.

Stromal tissue introduced prior to hematopoietic cell transplant, e.g., BMT, may be varied by: (1) administering the fetal liver and thymus tissue as a fluid cell suspension; (2) administering fetal liver or thymus stromal tissue but not both; (3) placing a stromal implant into other encapsulated, well-vascularized sites, or (4) using adult thymus or fetal spleen as a source of stromal tissue.

Tolerance to fully MHC mismatched renal allografts in chimeric swine

Overwhelming importance of major histocompatibility complex (MHC) class II matching for achieving tolerance of kidney transplants (KTx) in miniature swine has been demonstrated previously. When class II antigens are matched, long-term specific tolerance across MHC class I and minor antigens (MA) barrier, can uniformly be induced by a short course of cyclosporine. However, cyclosporine does not produce this effect across a full MHC barrier. Bone marrow transplantation (BMT) across single-haplotype class II MHC+MA barriers creates fully chimeric animals, as confirmed by FCM. These chimeras recover normal cellular immune function 2–3 months after BMT, as tested by MLR and CML. Four such chimeric animals (see Table 1, numbers 1–4) received kidney transplants from donors class II matched to BMT donors and fully mismatched to the recipients. A 12-day course of cyclosporine (10 mg/kg/day) was the only immunosuppression following kidney transplantation. All 4 pigs have maintained normal creatinine (Cr) values (<2 mg%) for longer than 300 days, and one recipient is alive over 3 years with good kidney function (Cr<2 mg%) and graft histology showing minimal borderline rejection. These results demonstrate that induction of tolerance to class II antigens by BMT allows a short course of cyclosporine to induce specific tolerance (as tested by skin grafts) to fully allogeneic kidney transplants. Subsequently, we have examined the specificity of this phenomenon by determining if single-haplotype class II+MA mismatched BMT will facilitate cyclosporine induced long-term acceptance of kidney transplants completely mismatched to both the recipient and BMT donor (Table 1, numbers 5–10). A 12-day course of cyclosporine allowed long-term survival of such kidney transplants in chimeric recipients. Animal #5 was still alive and clinically well, with normal Cr levels; histology however reveals borderline rejection. Animal #6 was sacrificed 18 months after kidney transplant, with deteriorating kidney function (Cr>11 mg%). Animal #7 was sacrificed at 6 months after kidney transplant due to sepsis, kidney transplants showed moderate tubulointestinal infiltrate without signs of vascular injury. Both long-term survivors (pigs #3 & 5) were recently tested for anti-donor reactivity. CML and MLR revealed specific unresponsiveness to the kidney transplant donor type cells. Pigs #8–10 received kidney transplant from outbred Yorkshire donors. These animals developed irreversible renal failure, starting shortly after cessation of the cyclosporine therapy.

residual T cells remained, often coated with antibody. In order to further suppress T cell function, a one-month course of treatment with an i.m. preparation of cyclosporine(CyA) in oil was added to the preparative regimen. This treatment led to therapeutic levels of cyclosporine during drug administration and to tapering levels over a period of 3 weeks after the drug was discontinued. The basic protocol for nonlethal preparative regimen was as follows: Cynomolgus monkeys weighing 6 to 10 kg. (Charles River Primates, Wilmington, Mass.) were treated with 300 Rads of WBI either as a single dose (#M393) on day −6 or as two fractions of 150 Rads each on days −6 and −5 (#M3093 and #M3293). 700 Rads of thymic irradiation was administered on day −1. Horse anti-human thymocyte globulin (ATG) (Upjohn) was administered at 50 mg/kg i.m. on days −2, −1 and 0. Orthotopic kidney transplantation was performed on day 0 through a midline incision using end to side anastamoses of the donor renal artery and renal vein into the recipient aorta and vena

TABLE 1

| # | RECIPIENT | BMT DONOR | KTx DONOR | OUTCOME (FUNCT./PATH.) |
|---|---|---|---|---|
| 1 | aa ($I^{aa}II^{aa}$) | aj ($I^{aa}II^{ac}$) | cc ($I^{cc}I^{cc}$) | sac 1y (good/normal) |
| 2 | ac ($I^{ac}II^{ac}$) | ag ($I^{ac}II^{ad}$) | dd ($I^{dd}II^{dd}$) | died > 2.5y (good/chronic rej) |
| 3 | ac ($I^{ac}II^{ac}$) | ag ($I^{ac}II^{ad}$) | dd ($I^{dd}II^{dd}$) | alive > 3y (good/border rej) |
| 4 | ac ($I^{ac}II^{ac}$) | ag ($I^{ac}II^{ad}$) | dd ($I^{dd}II^{dd}$) | sac 1y (good/normal) |
| 5 | aa ($I^{aa}II^{aa}$) | ah ($I^{aa}II^{ad}$) | cc ($I^{cc}II^{cc}$) | alive > 2.5y (good/border rej) |
| 6 | aa ($I^{aa}II^{aa}$) | ah ($I^{aa}II^{ad}$) | cc ($I^{cc}I^{cc}$) | sac > 1.5y (poor/chronic rej) |
| 7 | aa ($I^{aa}II^{aa}$) | aj ($I^{aa}II^{ac}$) | dd ($I^{dd}II^{dd}$) | sac 0.5y (good/infiltrate) |
| 8 | aa ($I^{aa}II^{aa}$) | aj ($I^{aa}II^{ac}$) | YORK ($I^?II^?$) | sac 30 d (poor/acute rej) |
| 9 | ac ($I^{ac}II^{ac}$) | ch ($I^{ac}II^{ad}$) | YORK ($I^?II^?$) | sac 70 d (poor/acute rej) |
| 10 | ac ($I^{ac}II^{ac}$) | ch ($I^{ac}II^{ad}$) | YORK ($I^?II^?$) | sac 38 d (poor/acute rej) | sac = sacrificed; rej = rejection

Thus, a short postoperative course of cyclosporine in MHC class II mismatched BMT recipients allows tolerance to be induced to kidney transplants that are class II matched to the BMT donor. Long-term unresponsiveness to kidney transplants that are fully mismatched to both the recipient and BMT donor can be achieved in some cases, apparently dependent on the degree of disparity at multiple loci (compare with the difference between inbred and outbred donors).

A short course of cyclosporine to suppress T cell function in primate allogeneic kidney transplantation.

The following experiment shows that mixed chimerism, obtained during a non-myeloablative protocol to achieve engraftment, is capable of producing multilineage lymphohematopoietic chimerism and long-term tolerance to renal allografts between fully MHC mismatched cynomolgus monkeys. Complete ablation of host lymphohematopoietic elements is neither necessary nor desirable when bone marrow transplantation is utilized as a tolerance-inducing regimen. Instead, it is advantageous to achieve a state of mixed chimerism, in which the presence of certain donor-derived elements induce specific tolerance, while host-type antigen presenting cells maintain normal immunocompetence.

It has been demonstrated in murine studies that removal of mature host T cells is important in order to achieve mixed chimerism. In initial studies using fully MHC mismatched cynomolgus monkeys, a variety of monoclonal antibodies were tested to mature T cell subsets (anti-CD4 and anti-CD8) as well as several sources of anti-thymocyte globulin (ATG) as T cell depleting reagents. Although these antibody treatments led to marked depletion of T cells in the peripheral blood, biopsies of lymph nodes demonstrated that cava, respectively, and using a ureteroureteral anastomosis for urinary drainage. Bone marrow was harvested from two donor ribs, prepared as a single cell suspension, and infused i.v. into the recipient at the end of the renal transplant. Treatment with cyclosporine (Sandimmun, 15 mg/kg/day, suspended in olive oil) i.m. was begun on day 0 and continued for 27 days.

Monkey #393 became pancytopenic on day 8, and required three blood transfusions with blood group matched, irradiated whole blood over the next two weeks. However, peripheral blood components recovered gradually thereafter, and were normal by day 30. Renal function has remained normal for over 250 days, and a biopsy on day 215 showed a normal kidney.

Sequential flow cytometric (FMC) analyses were performed on this animal utilizing a monoclonal anti-class I antibody previously determined to distinguish donor from host, and analyzing lymphoid, monocytic and neutrophil populations as determined by scatter profiles. Clear evidence for chimerism in all three subpopulations was detected first on day 10, and persisted at similarly high levels until cyclosporine treatment was discontinued on day 27. Thereafter, the levels of chimerism detected in each subpopulation decreased, but chimerism was still detectable by FCM among lymphocytes (1.5%) and monocytes (29%) as late as day 203, the last day tested. In addition, a bone marrow aspirate on day 203 showed 11.2% donor cells by FCM.

Mixed lymphocyte reactions performed pre-transplant and on day 159 post-transplant revealed a specific loss of anti-donor reactivity (Table 2).

| TIME | MEDIUM | AUTOLOGOUS | DONOR | 3RD PARTY #1 | 3RD PARTY #2 |
|---|---|---|---|---|---|
| Pre-Transplant (CPM) | 888 | 2434 | 5946 | 5571 | 6986 |
| Pre-Transplant (Stim. Index) | — | 1.0 | 3.3 | 3.0 | 3.9 |
| Day 159 (CPM) | 703 | 3410 | 2324 | 11298 | 9127 |
| Day 159 (Stim. Index) | — | 1.0 | 0.6 | 4.2 | 3.1 |

This result, combined with normal renal function and normal kidney histology without any additional exogenous immunosuppression since day 27, lead us to conclude that specific transplantation tolerance has been induced in this animal through the establishment of mixed chimerism. Two additional animals were treated by the same protocol, but with an intravenous preparation ofcyclosporine which led to an abrupt fall ofcyclosporine levels in the blood after discontinuation rather than gradual tapering of levels over a three-week period. One of these animals died of sepsis on day 12 during the period of aplasia, and the other lost evidence for chimerism after discontinuation ofcyclosporine and although still alive on day 100, has shown a course consistent with chronic rejection both by clinical and pathological criteria.

In order to reduce the toxicity of the preparative regimen, we have subsequently modified the irradiation protocol. In one animal (#3893) the WBI was decreased to 1.5 Gy. This animal failed to develop mixed chimerism and rejected the kidney transplant (Creatinine=12.1 on day 47). In two additional animals (#3093 and #3292) the WBI was maintained at 3.0 Gy, but was fractionated to 1.5 Gy on two successive days (−6 and −5) rather than administered as a single dose. Both of these animals developed mixed multi-lineage chimerism, first detectable on day 11 and day 20 respectively. They showed much less toxicity from the preparative regimen than did the animals receiving unfractionated irradiation, and both remain chimeric with normal renal function at the time of this writing (day 40 and day 25, respectively).

Pig To Monkey Kidney Xenotransplantation By A Mixed Chimerism Approach

The following experiment shows the induction of tolerance in monkeys to pig organs by means of a xenogeneic lymphohematopoietic chimerism approach which has previously been shown effective in concordant rodent systems. To date 16 Cynomolgus monkeys have received pig kidney transplants along with xenogeneic bone marrow from the same donor. The preparative regimen for these xenografts included: 1) conditioning with non-myeloablative whole body irradiation (WBI) and thymic irradiation; 2) removal of preformed mAbs by perfusion of monkey blood through a pig liver; 3) splenectomy; 4) T cell depletion with ATG and/or mAbs; and 5) postoperative immunosuppression with cyclosporine and in some animals anti-IgM mAbs. Ten animals have survived more than 4 days, with the longest surviving 13 days, with normal renal function to day 11. In this animal pig cells were detected in the peripheral blood only at day 10 post-transplant, suggesting transient xenogeneic chimerism. Two monkeys received only splenectomy and pig liver perfusion prior to the kidney xenograft. In one of these animals, in which no further immunosuppression was administered post-transplant, the kidney functioned for 3 days, then rapidly lost function, with complete rejection by day 5. Analysis of this monkey's sera by flow cytometry indicated return of high titers of IgM, which correlated with rejection. In the second animal cyclosporine 15 mg/kg/day iv and 15 deoxyspergualin (DSG) 6 mg/kg/day iv were administered post-transplant. The kidney functioned until day 7, then failed and was removed on day 8. Pathologic examination showed a focal inflammatory infiltrate in addition to patchy interstitial hemorrhage. The infiltrate contained approximately 20% T cells, as determined by staining with mAbs to CD3, CD4 and CD8. IgM natural antibodies were effectively removed during liver perfusion in this animal, and strikingly, they did not appear in the serum thereafter, IgG levels started to rise on day 7, correlating with the beginning of renal dysfunction. These results show 1) that natural antibody (IgM) responses can be effectively eliminated by components of the preparative regimen involving pig liver absorption and post-operative suppression with DSG; and 2) that T cell suppressive components of the preparative regimen (i.e., irradiation, cyclosporine and ATG) are required to prevent cellular and secondary (IgG) responses in these experiments.

Other Embodiments

Stromal tissue introduced prior to hematopoietic cell transplant, e.g., BMT, may be varied by: (1) administering the fetal liver and thymus tissue as a fluid cell suspension; (2) administering fatal liver or thymus stromal tissue but not both; (3) placing a stromal implant into other encapsulated, well-vascularized sites, or (4) using adult thymus or fetal spleen as a source of stromal tissue.

The methods described herein for inducing tolerance to, or promoting the acceptance of, an allogeneic antigen or allogeneic graft can be used where, as between the donor and recipient, there is any degree of mismatch at MHC loci or other loci which influence graft rejection. Preferably, there is a mismatch at at least one MHC locus or at at least one other locus that mediates recognition and rejection, e.g., a minor antigen locus. With respect to class I and class II MHC loci, the donor and recipient can be: matched at class I and mismatched at class II; mismatched at class I and matched at class II; mismatched at class I and mismatched at class II; matched at class I, matched at class II. In any of these combinations other loci which control recognition and rejection, e.g., minor antigen loci, can be matched or mismatched. As stated above, it is preferable that there is mismatch at least one locus. Mismatched at MHC class I means mismatched for one or more MHC class I loci, e.g., in the case of humans, mismatched at one or more of HLA-A, HLA-B, or HLA-C, or in the case of swine, mismatch at one or more SLA class I loci, e.g., the swine A or B loci. Mismatched at MHC class II means mismatched at one or more MHC class II loci, e.g., in the case of humans, mismatched at one or more of a DP $\alpha$, a DP$\beta$, a DQ $\alpha$, a DQ $\beta$, a DR $\alpha$, or a DR $\beta$, or in the case of swine, mismatch at one or SLA class II loci, e.g., mismatch at DQ $\alpha$ or $\beta$, or DR $\alpha$ or $\beta$.

The methods described herein for inducing tolerance to an allogeneic antigen or allogeneic graft can be used where, as between the donor and recipient, there is any degree of reactivity in a mixed lymphocyte assay, e.g., wherein there is no, low, intermediate, or high mixed lymphocyte reactivity between the donor and the recipient. In preferred embodiments mixed lymphocyte reactivity is used to define mismatch for class II, and the invention includes methods for performing allogeneic grafts between individuals with any degree of mismatch at class II as defined by a mixed lymphocyte assay. Serological tests can be used to determine mismatch at class I or II loci and the invention includes methods for performing allogeneic grafts between individuals with any degree of mismatch at class I and or II as measured with serological methods. In a preferred embodiment, the invention features methods for performing allogeneic grafts between individuals which, as determined by serological and or mixed lymphocyte reactivity assay, are mismatched at both class I and class II.

The methods of the invention are particularly useful for replacing a tissue or organ afflicted with a neoplastic disorder, particularly a disorder which is resistant to normal modes of therapy, e.g., chemotherapy or radiation therapy. Methods of the invention can be used for inducing tolerance to a graft, e.g., an allograft, e.g., an allograft from a donor which is mismatched at one or more class I loci, at one or more class II loci, or at one or more loci at each of class I and class II. In preferred embodiments: the graft includes tissue from the digestive tract or gut, e.g., tissue from the stomach, or bowel tissue, e.g., small intestine, large intestine, or colon; the graft replaces a portion of the recipient's digestive system e.g., all or part of any of the digestive tract or gut, e.g., the stomach, bowel, e.g., small intestine, large intestine, or colon.

Tolerance, as used herein, refers not only to complete immunologic tolerance to an antigen, but to partial immunologic tolerance, i.e., a degree of tolerance to an antigen which is greater than what would be seen if a method of the invention were not employed.

As is discussed herein, it is often desirable to expose a graft recipient to irradiation in order to promote the development of mixed chimerism. The inventor has discovered that it is possible to induce mixed chimerism with less radiation toxicity by fractionating the radiation dose, i.e., by delivering the radiation in two or more exposures or sessions. Accordingly, in any method of the invention calling for the irradiation of a recipient, e.g., a primate, e.g., a human, recipient, of a xenograft or allograft, the radiation can either be delivered in a single exposure, or more preferably, can be fractionated into two or more exposures or sessions. The sum of the fractionated dosages is preferably equal, e.g., in rads or Gy, to the radiation dosage which can result in mixed chimerism when given in a single exposure. The fractions are preferably approximately equal in dosage. For example, a single dose of 700 rads can be replaced with, e.g., two fractions of 350 rads, or seven fractions of 100 rads. Hyperfractionation of the radiation dose can also be used in methods of the invention. The fractions can be delivered on the same day, or can be separated by intervals of one, two, three, four, five, or more days. Whole body irradiation, thymic irradiation, or both, can be fractionated.

The inventor has also discovered that much or all of the preparative regimen can be delivered or administered to a recipient, e.g., an allograft or xenograft recipient, within a few days, preferably within 72, 48, or 24 hours, of transplantation of tolerizing stem cells and/or the graft. This is particularly useful in the case of humans receiving grafts from cadavers. Accordingly, in any of the methods of the invention calling for the administration of treatments prior to the transplant of stem cells and/or a graft, e.g., treatments to inactivate or deplete host antibodies, treatments to inactivate host T cells or NK cells, or irradiation, the treatment(s) can be administered, within a few days, preferably within 72, 48, or 24 hours, of transplantation of the stem cells and/or the graft. In particular, primate, e.g., human, recipients of allografts can be given any or all of treatments to inactivate or deplete host antibodies, treatments to inactivate host T cells or NK cells, or irradiation, within a few days, preferably within 72, 48, or 24 hours, of transplantation of stem cells and/or the graft. For example, treatment to deplete recipient T cells and/or NK cells, e.g., administration of ATG, can be given on day −2, −1, and 0, and WBI, thymic irradiation, and stem cell, e.g., bone marrow stem cells, administered on day 0. (The graft, e.g., a renal allograft, is transplanted on day 0).

Methods of the invention can include recipient splenectomy.

As is discussed herein, hemoperfusion, e.g., hemoperfusion with a donor organ, can be used to deplete the host of natural antibodies. Other methods for depleting or otherwise inactivating natural antibodies can be used with any of the methods described herein. For example, drugs which deplete or inactivate natural antibodies, e.g., deoxyspergualin (DSG) (Bristol), or anti-IgM antibodies, can be administered to the recipient of an allograft or a xenograft. One or more of, DSG (or similar drugs), anti-IgM antibodies, and hemoperfusion, can be used to deplete or otherwise inactivate recipient natural antibodies in methods of the invention. DSG at a concentration of 6 mg/kg/day, i.v., has been found useful in suppressing natural antibody function in pig to cynomolgus kidney transplants.

Some of the methods described herein use lethal irradiation to create hematopoietic space, and thereby prepare a recipient for the administration of allogeneic, xenogeneic, syngeneic, or genetically engineered autologous, stem cells. In any of the methods described herein, particularly primate or clinical methods, it is preferable to create hematopoietic space for the administration of such cells by non-lethal means, e.g., by administering sub-lethal doses of irradiation, bone marrow depleting drugs, or antibodies. The use of sublethal levels of bone marrow depletion allows the generation of mixed chimerism in the recipient. Mixed chimerism is generally preferable to total or lethal ablation of the recipient bone marrow followed by complete reconstitution of the recipient with administered stem cells.

Alternative methods for the inactivation of thymic T cells are also included in embodiments of the invention. Some of the methods described herein include the administration of thymic irradiation to inactivate host thymic-T cells or to otherwise diminish the host's thymic-T cell mediated responses to donor antigens. It has been discovered that the thymic irradiation called for in allogeneic or xenogeneic methods of the invention can be supplemented with, or replaced by, other treatments which diminish (e.g., by depleting thymic-T cells and/or down modulating one or more of the T cell receptor (TCR), CD4 co-receptor, or CD8 co-receptor) the host's thymic-T cell mediated response. For example, thymic irradiation can be supplemented with, or replaced by, anti-T cell antibodies (e.g., anti-CD4 and/or anti-CD8 monoclonal antibodies) administered a sufficient number of times, in sufficient dosage, for a sufficient period of time, to diminish the host's thymic-T cell mediated response.

For best results, anti-T cell antibodies should be administered repeatedly. E.g., anti-T cell antibodies can be administered one, two, three, or more times prior to donor bone marrow transplantation. Typically, a pre-bone marrow transplantation dose of antibodies will be given to the patient about 5 days prior to bone marrow transplantation. Additional, earlier doses 6, 7, or 8 days prior to bone marrow transplantation can also be given. It may be desirable to administer a first treatment then to repeat pre-bone marrow administrations every 1–5 days until the patient shows excess antibodies in the serum and about 99% depletion of peripheral T cells and then to perform the bone marrow transplantation. Anti-T cell antibodies can also be administered one, two, three, or more times after donor bone marrow transplantation. Typically, a post-bone marrow transplant treatment will be given about 2–14 days after bone marrow transplantation. The post bone marrow administration can be repeated as many times as needed. If more than one administration is given the administrations can be spaced about 1 week apart. Additional doses can be given if the patient appears to undergo early or unwanted T cell recovery. Preferably, anti-T cell antibodies are administered at least once (and preferably two, three, or more times) prior to donor bone marrow transplantation and at least once (and preferably two, three, or more times) after donor bone marrow transplantation.

The following experiments show that additional T cell-depleting antibodies can replace thymic irradiation in a non-myeloablative conditioning regimen and allow allogeneic bone marrow engraftment and donor-specific tolerance induction.

A low toxicity, non-myeloablative conditioning regimen that allows allogeneic bone marrow engraftment and donor-specific tolerance induction in mice has been previously described. A regimen which includes pre-treatment with depleting doses of anti-CD4 and anti-CD8 monoclonal antibodies on day −5, administration of 3 Gy whole body irradiation and 7 Gy of thymic irradiation on day 0 followed by administration of fully MHC-mismatched donor bone marrow cells, allows the induction of permanent mixed chimerism and skin graft tolerance. The thymic irradiation step in this protocol was replaced with additional anti-CD4 and anti-CD8 monoclonal antibody treatment. Multilineage chimerism was compared in B10 (H-$2^b$) mice receiving allogeneic (B10.A, H-$2^a$) bone marrow transplantation on day 0 following 3 Gy whole body irradiation with or without thymic irradiation, and treatment with monoclonal antibodies by a variety of schedules pre and post-bone marrow transplantation. Most (50 of 52) animals that either received thymic irradiation or that received at least two pre-bone marrow transplantation monoclonal antibody treatments demonstrated long-term multilineage peripheral blood mixed allogeneic chimerism (as demonstrated by flow cytometric analysis). In contrast, only 1 of 8 animals receiving only one pre-bone marrow transplantation monoclonal antibody treatment without thymic irradiation developed lasting (more than 20 weeks) mixed chimerism. All chimeric animals accepted donor skin grafts for more than 100 days and rejected third party BALB/c grafts within 14 days. Therefore, mixed chimerism and donor-specific skin graft acceptance could be induced without the use of thymic irradiation if at least 2 pre-bone marrow transplantation monoclonal antibody treatments were given. (The monoclonal antibody treatments were spaced about 5 days apart with the final treatment 1 day prior to bone marrow transplantation.) However, levels of donor T cell reconstitution were highest in animals receiving thymic irradiation or receiving additional anti-T cell monoclonal antibody treatments following bone marrow transplantation. Eleven of 20 mice receiving two pre-bone marrow transplantation monoclonal antibody treatments (the monoclonal antibody treatments were spaced about 5 days apart with the final treatment 1 day prior to bone marrow transplantation) and no thymic irradiation showed relatively low levels of donor T cell reconstitution (less than 20% donor, more than 80% host) at 6 weeks, and 9 of these showed a marked loss of donor cells in all lineages by 20 weeks. In contrast, 12 of 12 similarly-treated mice receiving 1 or 2 additional post-bone marrow transplantation monoclonal antibody treatments (the monoclonal antibody treatments were spaced about 7 days apart with the first treatment 7 day after bone marrow transplantation) showed high levels of donor T cell reconstitution at 6 weeks (mean 86±12% donor), and high levels of donor reconstitution persisted in all lineages at 20 weeks. Thus, a second dose of pre-bone marrow transplantation T cell-depleting monoclonal antibodies can replace thymic irradiation and allow tolerance induction in our regimen, but additional monoclonal antibodies administered at one and two weeks post-bone marrow transplantation may increase the ability to reliably induce durable mixed chimerism and tolerance. The capacity of repeated anti-T cell monoclonal antibody treatments to replace thymic irradiation in this regime most likely reflects their ability to deplete host thymocytes that escape depletion by the initial monoclonal antibody treatment. These monoclonal antibodies deplete most host T cells and induce down-modulation of both TCR and CD4 and CD8 co-receptors on the few remaining cells. In these animals, early migration of donor bone marrow-derived cells to the host thymus is associated with complete clonal deletion of mature host-type thymocytes with TCR that recognize donor antigens. Although a small population of host T cells with such TCR persists in the spleens of chimeras, these cells are anergic to stimulation through their TCR. These cells may have escaped depletion by down-modulating CD4 or CD8 after monoclonal antibody treatment. Thus, this relatively non-toxic regime achieves pluripotent hematopoietic stem cell engraftment and specific tolerance by ablating most of the existing T cell repertoire and allowing new T cell development in the presence of intrathymic donor antigen, and by inducing anergy among the few remaining host T cells in the periphery.

Some of the methods herein include the administration of hematopoietic stem cells to a recipient. In many of those methods, hematopoietic stem cells are administered prior to or at the time of the implantation of a graft (an allograft or a xenograft), the primary purpose of the administration of hematopoietic stem cells being the induction of tolerance to the graft. The inventors have found that one or more subsequent administrations (e.g., a second, third, fourth, fifth, or further subsequent administration) of hematopoietic stem cells can be desirable in the creation and/or maintenance of tolerance. Thus, the invention also includes methods in which hematopoietic stem cells are administered to a recipient, e.g., a primate, e.g., a human, which has previously been administered hematopoietic stem cells as part of any of the methods referred to herein.

While not wishing to be bound by theory the inventor believes that repeated stem cell administration may promote chimerism and possibly long-term deletional tolerance in graft recipients. Accordingly, any method referred to herein which includes the administration of hematopoietic stem cells can further include multiple administrations of stem cells. In preferred embodiments: a first and a second administration of stem cells are provided prior to the implantation of a graft; a first administration of stem cells is provided prior to the implantation of a graft and a second administration of stem cells is provided at the time of implantation of the graft. In other preferred embodiments: a first administration of stem cells is provided prior to or at the time of implantation of a graft and a second administration of stem cells is provided subsequent to the implantation of a graft. The period between administrations of hematopoietic stem cells can be varied. In preferred embodiments a subsequent administration of hematopoietic stem cell is provided: at least two days, one week, one month, or six months after the previous administration of stem cells; at least two days, one week, one month, or six months after the implantation of the graft.

The method can further include the step of administering a second or subsequent dose of hematopoietic stem cells: when the recipient begins to show signs of rejection, e.g., as evidenced by a decline in function of the grafted organ, by a change in the host donor specific antibody response, or by a change in the host lymphocyte response to donor antigen; when the level of chimerism decreases; when the level of chimerism falls below a predetermined value; when the level of chimerism reaches or falls below a level where staining with a monoclonal antibody specific for a donor PBMC antigen is equal to or falls below staining with an isotype control which does not bind to PBMC's, e.g. when the donor specific monoclonal stains less than 1–2% of the cells; or generally, as is needed to maintain tolerance or otherwise prolong the acceptance of a graft. Thus, method of the invention can be modified to include a further step of determining if a subject which has received a one or more administrations of hematopoietic stem cells is in need of a subsequent administration of hematopoietic stem cells, and if so, administering a subsequent dose of hematopoietic stem cells to the recipient.

Any of the methods referred to herein can include the administration of agents, e.g., 15-deoxyspergualin, mycophenolate mofetil, brequinar sodium, or similar agents, which inhibit the production, levels, or activity of antibodies in the recipient. One or more of these agents can be administered: prior to the implantation of donor tissue, e.g., one, two, or three days, or one, two, or three weeks before implantation of donor tissue; at the time of implantation of donor tissue; or after implantation of donor tissue, e.g., one, two, or three days, or one, two or three weeks after, implantation of a graft.

The administration of the agent can be initiated: when the recipient begins to show signs of rejection, e.g., as evidenced by a decline in function of the grafted organ, by a change in the host donor specific antibody response, or by a change in the host lymphocyte response to donor antigen; when the level of chimerism decreases; when the level of chimerism falls below a predetermined value; when the level of chimerism reaches or falls below a level where staining with a monoclonal antibody specific for a donor PBMC antigen is equal to or falls below staining with an isotype control which does not bind to PBMC's, e.g. when the donor specific monoclonal stains less than 1–2% of the cells; or generally, as is needed to maintain tolerance or otherwise prolong the acceptance of a graft.

The period over which the agent is administered (or the period over which clinically effective levels are maintained in the subject) can be long term, e.g., for six months or more or a year or more, or short term, e.g., for less than a year, more preferably six months or less, more preferably one month or less, and more preferably two weeks or less. The period will generally be at least about one week and preferably at least about two weeks in duration. In preferred embodiments the period is two or three weeks long.

Preferred embodiments include administration of 15-deoxyspergualin (6 mg/kg/day) for about two weeks beginning on the day of graft implantation.

Some of the methods referred to herein include steps in which antibodies, e.g., preformed natural antibodies, are removed from the blood of a recipient. For example, in some methods antibodies are removed by hemoperfusion of an organ from the donor species. The inventor has discovered that an α1–3 galactose linkage epitope-affinity matrix, e.g., in the form of an affinity column, is useful for removing antibodies from the recipient's blood. Accordingly, the use of an α1–3 galactose linkage epitope-affinity matrix, e.g., matrix bound linear B type VI carbohydrate, can be added to any method referred to herein and can be used in addition to or in place of any antibody perfusion or removal technique, e.g., organ perfusion, in any method referred to herein.

Some of the methods referred to herein include the administration of hematopoietic stem cells to a recipient. In many of those methods hematopoietic stem cells are administered prior to or at the time of the administration of a graft (an allograft or a xenograft), the primary purpose of the administration of hematopoietic stem cells being the induction of tolerance to the graft. The inventors have found that administration of one or more cytokines, preferably a cytokine from the species from which the stem cells are derived, can promote tolerance or otherwise prolong acceptance of a graft. Thus, the invention also includes methods in a subject which has previously been administered donor hematopoietic stem cells, is administered one or more cytokine, e.g., a donor-species cytokine.

Although not wishing to be bound by theory, the inventor believes that the cytokines, particularly donor species cytokines, promote the engraftment and/or function of donor stem cells or their progeny cells. Accordingly, any method referred to herein which includes the administration of hematopoietic stem cells can further include the administration of a cytokine, e.g., SCF, IL-3, or GM-CSF. In preferred embodiments the cytokine one which is species specific in its interaction with target cells.

Administration of a cytokine can begin prior to, at, or after the implantation of a graft or the implantation of stem cells.

The method can further include the step of administering a first or subsequent dose of a cytokine to the recipient: when the recipient begins to show signs of rejection, e.g., as evidenced by a decline in function of the grafted organ, by a change in the host donor specific antibody response, or by a change in the host lymphocyte response to donor antigen; when the level of chimerism decreases; when the level of chimerism falls below a predetermined value; when the level of chimerism reaches or falls below a level where staining with a monoclonal antibody specific for a donor PBMC antigen is equal to or falls below staining with an isotype control which does not bind to PBMC's, e.g. when the donor specific monoclonal stains less than 1–2% of the cells; or generally, as is needed to maintain tolerance or otherwise prolong the acceptance of a graft. Thus, method of the invention can be modified to include a further step of determining if a subject is in need of cytokine therapy and if so, administering a cytokine.

The period over which the cytokine(s) is administered (or the period over which clinically effective levels are maintained in the subject) can be long term, e.g., for six months of more or a year or more, or short term, e.g., for a year or less, more preferably six months or less, more preferably one month or less, and more preferably two weeks or less. The period will generally be at least about one week and preferably at least about two weeks in duration.

In preferred embodiments the recipient is a primate, e.g., a human, and the donor is from a different species, e.g., the donor is a pig and: pig SCF is administered; pig IL-3 is administered; a combination of pig SCF and pig IL-3 is administered; a pig specific hematopoiesis enhancing factor, e.g., pig GM-SCF, is administered, e.g., after the implantation of stem cells, e.g., about a month after the implantation of stem cells.

A particularly preferred embodiment combines a short course, e.g., about a month, of cyclosporine or a similar agent, a short course, e.g., about two weeks, of 15-deoxyspergualin or a similar agent, and a short course, e.g., about two weeks, of donor specific cytokines, e.g., SCF and IL-3. In Cynomolgus monkeys receiving pig grafts and pig stem cells, treatment which included the combination of cyclosporine (15 mg/kg/day for 28 days), 15-deoxyspergualin (6 mg/kg/day for two weeks), and recombinant pig cytokines (SCF and IL-3, each at 10 μg/kg/day, i.v., for two weeks) was found to be useful. Administration began at the time of graft implant. (The monkeys were also given a preparative regime consisting of 3×100cGy total body irradiation on day −6, and −5 and hemoperfusion with a pig liver just prior to stem cell administration.)

An anti-CD2 antibody, preferably a monoclonal, e.g., BTI-322, or a monoclonal directed at a similar or overlapping epitope, can be used in addition to or in place of any anti-T cell antibodies (e.g., ATG) in any method referred to herein.

Other embodiments are within the following claims.

What is claimed is:

1. A method of inducing tolerance in a recipient primate of a first species to a graft obtained from a mammal of a second species comprising:

introducing into said recipient, hematopoietic stem cells of the second species, implanting said graft in said recipient;

inactivating T cells of said recipient; and, administering to said recipient a short course of an immunosuppressive agent, which agent is other than an anti-T cell antibody, wherein said short course is equal to or less than 120 days, thereby inducing tolerance to the graft.

2. The method of claim 1, wherein said short course of immunosuppressive agent is equal to or less than 20 days.

3. The method of claim 1, wherein the duration of said short course of an immunosuppressive agent is equal to or less than 30 days.

4. The method of claim 1, wherein the duration of said short course is equal to or less than 40 days.

5. The method of claim 1, wherein said short course of immunosuppressive agent is equal to or less than 50 days.

6. The method of claim 1, wherein said short course of immnunosuppressive agent is about one month.

7. The method of claim 1, wherein said short course of an immunosuppressive agent is generally administered at about the time hematopoietic stem cells are given to said recipient.

8. The method of claim 1, wherein said short course an immunosuppressive agent is administered in the absence of a steroid drug.

9. The method of claim 1, wherein said immunosuppressive agent is administered in the absence of prednisone.

10. The method of claim 1, therein said short course of an immunosuppressive agent includes the administration of cyclosponrine A.

11. The method of claim 1, wherein said short course of an immnunosuppressive agent includes the administration of FK506.

12. The method of claim 1, wherein, said short course of an immunosuppressive agent includes, the administration of rapamycin.

13. The method of claim 1, wherein said recipient is a human.

14. The method of claim 1, wherein said recipient is a human and said graft is from a swine.

15. The method of claim 1, wherein said recipient is a human and said graft is from a miniature swine.

16. The method of claim 1, wherein said stem cells are bone marrow stem cells.

17. The method of claim 1, wherein said recipient is given a second administration of hematopoietic stem cells.

18. The method of claim 1, wherein said graft is chosen from the group consisting of a kidney a heart, and a liver.

19. The method of claim 1, wherein said inactivation of T cells includes introducing into said recipient an antibody which binds to mature T cells of said recipient.

20. The method of claim 19, wherein said T cell antibodies are administered prior to said hematopoietic stem cells.

21. The method of claim 1, wherein said inactivation of T cells includes down modulating one or more of the T cell receptor, CD4 co-receptor, or CD8 co-receptor.

22. The method of claim 1, wherein the method further comprises creating hematopoietic space prior to hematopoietic stem cell transplantation in said recipient.

23. The method of claim 22, wherein hematopoietic space is created by exposing the recipient to sub-lethal irradiation.

24. The method of claim 22, wherein hematopoietic space is created by exposing the recipient to 100–400 rads of whole body irradiation.

25. The method of claim 1, wherein said recipient is a human and cyclosporine is administered for less than 60 days.

26. A method of inducing tolerance in a recipient primate to a graft obtained from a donor primate of the same species comprising:

introducing into said recipient primate, hematopoietic stem cells of said donor;

implanting said graft in said recipient;

inactivating T cells of said recipient; and, administering to said recipient a short course of an immunosuppressive agent, which agent is other than an anti-T cell antibody, wherein said short course is equal to or less than 120 days, thereby inducing tolerance to the graft.

27. The method of claim 26, wherein said short course of immunosuppressive agent is equal to or less than 20 days.

28. The method of claim 26, wherein the duration of said short course of an immunosuppressive agent is equal to or less than 30 days.

29. The method of claim 26, wherein the duration of said short course is equal to or less than 40 days.

30. The method of claim 26, wherein said short course of immunosuppressive agent is equal to or less than 50 days.

31. The method of claim 26, wherein said short course of imnmnunosuppressive agent is about one month.

32. The method of claim 26, wherein said short course of an immunosuppressive agent is generally administered at about the time hematopoietic stem cells are given to said recipient.

33. The method of claim 26, wherein said short course of an immunosuppressive agent is administered in the absence of a steroid drug.

34. The method of claim 33, wherein said immunosuppressive agent is administered in the absence of prednisone.

35. The method of claim 26, wherein said short course of an immunosuppressive agent includes the administration cyclosporine A.

36. The method of claim 26, wherein said short course of an immunosuppressive agent includes the administration of FK506.

37. The method of claim 26, wvherein, said short course of an immunosuppressive agent includes the administration of rapamycin.

38. The method of claim 26, wherein said recipient is a human.

39. The method of claim 26, wherein said stem cells are bone marrow stem cells.

40. The method of claim 26, wherein said recipient is given a second administration of hematopoietic stem cells.

41. The method of claim 26, wherein said graft is chosen from the group consisting of a kidney, a heart, and a liver.

42. The method of claim 26, wherein said inactivation of T cells includes introducing into said recipient an antibody which binds to mature T cells of said recipient.

43. The method of claim 42, wherein said T cell antibodies are administered prior to said hematopoietic stem cells.

44. The method of claim 26, wherein said inactivation of T cells includes down modulating one or more of the T cell receptor, CD4 co-receptor, or CD8 co-receptor.

45. The method of claim 26, wherein said recipient and the donor of said hematopoietic stem cells are mismatched at one or more class II loci.

46. The method of claim 26, wherein said recipient and the donor of said hematopoietic stem cells are mismatched at class I and class II.

47. The method of claim 26, wherein the donor of the graft and said recipient are mismatched at one or more class II loci.

48. The method of claim 26, wherein the method further comprises creating hematopoietic space prior to hematopoietic stem cell transplantation in said recipient.

49. The method of claim 48, wherein hematopoietic space is created by exposing the recipient to sub-lethal irradiation.

50. The method of claim 48, wherein hematopoietic space is created by exposing the recipient to 100–400 rads of whole body irradiation.

51. A method of diminishing or inhibiting the activity of thymic or lymph node T cells in a recipient primate which receives a graft from a donor mammal, comprising:

introducing into said recipient primate, hematopoietic stem cells of said donor;

inactivating T cells of said recipient;

administering to said recipient, a short course of an immunosuppressive agent, wherein said agent is a chemical agent and is other than an anti-T cell antibody, sufficient to inactivate thymic or lymph node T cells; and, transplanting said graft into said recipient, wherein said short course of an immunosuppressive agent is equal to or less than 120 days, thereby diminishing or inhibiting the activity of thymic or lymph node T cells in a recipient primate to said graft.

52. The method of claim 51, wherein, said short course is begun before or at about the time the treatment to induce tolerance is begun.

53. The method of claim 51, wherein said recipient and said donor are of the same species and are mismatched at a first locus which affects graft rejection, and matched, or tolerant of a mismatch, at a second locus which affects graft rejection.

54. The method of claim 51, wherein the donor of the graft and said recipient are from the same species and the donor and said recipient are mismatched at one or more class II loci.

55. The method of claim 51, wherein said short course of an immunosuppressive agent is administered in the absence of a steroid drug.

56. The method of claim 51, wherein said immunosuppressive agent is administered in the absence of prednisone.

57. The method of claim 51, wherein said short course of an immunosuppressive agent includes the administration of cyclosporine A.

58. The method of claim 51, wherein said short course of an immunosuppressive agent includes the administration of FK506.

59. The method of claim 51, wherein, said short course of an immunosuppressive agent includes the administration of rapamycin.

60. The method of claim 51, wherein said recipient is a human and said graft is from a human.

61. The method of claim 51, wherein said recipient is a human and said graft is from a swine.

62. The method of claim 51, wherein said recipient is a human and said graft is from a miniature swine.

63. The method of claim 51, wherein said stem cells are bone marrow cells.

64. The method of claim 51, wherein said recipient and the donor of said hematopoietic stem cells are mismatched at one or more class II loci.

65. The method of claim 51, wherein said recipient and the donor of said hematopoietic stem cells are mismatched at class I and class II.

66. The method of claim 51, wherein the method further comprises creating hematopoietic space prior to hematopoietic stem cell transplantation in said recipient.

67. The method of claim 66, wherein hematopoietic space is created by exposing the recipient to sub-lethal irradiation.

68. The method of claim 66, wherein hematopoietic space is created by exposing the recipient to 100–400 rads of whole body irradiation.

69. The method of claim 66, wherein said recipient is given a second administration of hematopoietic stem cells.

70. The method of claim 51, wherein said graft is chosen from the group consisting of a kidney, a heart, and a liver.

71. The method of claim 51, wherein said short course of immunosuppressive agent is about one month.

72. The method of claim 51, wherein said short course of immunosuppressive agent is equal to or less than 20 days.

73. The method of claim 51, wherein said short course of immunosuppressive agent is equal to or less than 30 days.

74. The method of claim 51, wherein said short course of immunosuppressive agent is equal to or less than 40 days.

75. The method of claim 51, wherein said short course of immunosuppressive agent is equal to or less than 30 days.

76. The method of claim 51, wherein said inactivation of T cells includes introducing into said recipient an antibody which binds to mature T cells of said recipient.

77. The method of claim 51, wherein said T cell antibodies are administered prior to said hematopoietic stem cells.

78. The method of claim 51, wherein said inactivation of T cells includes down modulating one or more of the T cell receptor, CD4 co-receptor, or CD8 co-receptor.

79. The method of claim 51, wherein said recipient and donor are of the same species and are mismatched at one or more class II loci.

* * * * *

SEQUENCE LISTING ( 1 ) GENERAL INFORMATION:

( i i i ) NUMBER OF SEQUENCES: 4

( 2 ) INFORMATION FOR SEQ ID NO: 1:

( i ) SEQUENCE CHARACTERISTICS:
        ( A ) LENGTH: 22
        ( B ) TYPE: nucleic acid
        ( C ) STRANDEDNESS: single
        ( D ) TOPOLOGY: linear ( x i ) SEQUENCE DESCRIPTION: SEQ ID NO: 1:

CCACAGGCCT GATCCCTAAT GG      2 2

( 2 ) INFORMATION FOR SEQ ID NO: 2:

( i ) SEQUENCE CHARACTERISTICS:
        ( A ) LENGTH: 23
        ( B ) TYPE: nucleic acid
        ( C ) STRANDEDNESS: single
        ( D ) TOPOLOGY: linear ( x i ) SEQUENCE DESCRIPTION: SEQ ID NO: 2:

AGCATAGCAG GAGCCTTCTC ATG      2 3

( 2 ) INFORMATION FOR SEQ ID NO: 3:

( i ) SEQUENCE CHARACTERISTICS:
        ( A ) LENGTH: 27
        ( B ) TYPE: nucleic acid
        ( C ) STRANDEDNESS: single
        ( D ) TOPOLOGY: linear ( x i ) SEQUENCE DESCRIPTION: SEQ ID NO: 3:

GGCCCACACT CGCTGAGGTA TTTCGTC      2 7

( 2 ) INFORMATION FOR SEQ ID NO: 4:

( i ) SEQUENCE CHARACTERISTICS:
        ( A ) LENGTH: 25
        ( B ) TYPE: nucleic acid
        ( C ) STRANDEDNESS: single
        ( D ) TOPOLOGY: linear ( x i ) SEQUENCE DESCRIPTION: SEQ ID NO: 4:

GCCAGAGATC ACCTGAATAG TGTGA      2 5